(12) United States Patent
Ogasawara et al.

(10) Patent No.: US 8,784,593 B2
(45) Date of Patent: Jul. 22, 2014

(54) METHOD FOR MANUFACTURING ABSORPTIVE ARTICLE

(75) Inventors: Yoshikazu Ogasawara, Kagawa (JP); Noriaki Ito, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 432 days.

(21) Appl. No.: 13/139,126

(22) PCT Filed: Dec. 2, 2009

(86) PCT No.: PCT/JP2009/070255
§ 371 (c)(1),
(2), (4) Date: Aug. 2, 2011

(87) PCT Pub. No.: WO2010/071023
PCT Pub. Date: Jun. 24, 2010

(65) Prior Publication Data
US 2011/0277921 A1    Nov. 17, 2011

(30) Foreign Application Priority Data
Dec. 18, 2008   (JP) .................................. 2008-322779

(51) Int. Cl.
A61F 13/15   (2006.01)
(52) U.S. Cl.
USPC ......................................... 156/204; 156/269
(58) Field of Classification Search
None
See application file for complete search history.

(56) References Cited

U.S. PATENT DOCUMENTS 6,461,344 B1 *  10/2002  Widlund et al. .............. 604/390

FOREIGN PATENT DOCUMENTS

| JP | 2004-113591 A | 4/2004 |
| JP | 2005-065971 A | 3/2005 |
| JP | 2008-253633 A | 10/2008 |
| JP | 2008-272250 A | 11/2008 |
| WO | WO 2007073247 A1 * | 6/2007 |
| WO | WO 2008079061 A1 * | 7/2008 |

OTHER PUBLICATIONS

International Search Report for PCT/JP2009/070255 mailed Mar. 2, 2010.

* cited by examiner

*Primary Examiner* — Barbara J Musser
(74) *Attorney, Agent, or Firm* — Lowe Hauptman & Ham LLP

(57) ABSTRACT

A method for manufacturing an absorbent article includes joining, one longitudinal end portion of a main absorbent body base material to a back-side band base material and another longitudinal end portion of the absorbent body base material to the abdominal-side band base material, folding the main absorbent body base material and overlapping the back-side band base material with the abdominal-side band base material, temporarily joining the overlapped back-side band base material and abdominal-side band base material cutting the temporarily joined back-side band base material and abdominal-side band base material and forming a back-side band base material piece and an abdominal-side band base material piece, and transporting the back-side band base material piece, the abdominal-side band base material piece and the main absorbent body base material in a transport direction with the back-side band base material piece and the abdominal-side band base material piece in a temporarily joined state.

14 Claims, 12 Drawing Sheets

METHOD FOR MANUFACTURING ABSORPTIVE ARTICLE

RELATED APPLICATIONS

The present application is a National Phase of International Application Number PCT/JP2009/070255, filed Dec. 2, 2009 and claims priority from, Japanese Application Number 2008-322779, filed Dec. 18, 2008.

TECHNICAL FIELD

The present invention relates to a method for manufacturing an absorbent article. More particularly, the invention relates to a method for manufacturing an absorbent article including a main absorbent body set against the crotch when worn, a back-side band positioned on the back side when worn, and an abdominal-side band positioned on the abdominal-side when worn, the absorbent article has formed, in a direction that intersects the longitudinal direction or the main absorbent body, protruding portions that protrude from the ends of the main absorbent body at the back-side band and the abdominal-side band, respectively.

BACKGROUND ART

Absorbent articles such as disposable diapers are well known. To give an explanation on one configuration of an absorbent article, there is an absorbent article including an absorbent body that absorbs liquid, and having a main absorbent body that is put against the crotch when worn, a back-side band that intersects the main absorbent body at one longitudinal end portion of the main absorbent article and that is positioned on the back side when worn, an abdominal-side band that intersects the absorbent body at another longitudinal end portion of the absorbent article and that is positioned on the abdominal-side when worn. There is also an absorbent article that has two protruding portions protruding from both ends, formed on the back-side band and the abdominal-side band, respectively of the main absorbent body in a direction intersecting the longitudinal direction of the main absorbent body.

The manufacturing line for this absorbent article with the above configuration has, while transporting the continuous back-side band and abdominal-side band base materials in the transport direction, a process of joining one longitudinal end portion of the main absorbent body base material to the above-mentioned back-side band base material and a process of joining the other longitudinal end portion to the above-mentioned abdominal-side band base material, so that the transport direction intersects the longitudinal direction of the main absorbent body base material. With this process, the main absorbent body base material is transported in the transport direction that intersects the longitudinal direction thereof, in a state spanning across the back-side band base material and the abdominal-side band base material. (For example, refer to FIG. 5)

Further, the above-described manufacturing line has a process of overlapping the back-side band base material with the abdominal-side band base material so that the main absorbent body base material is folded, after joining the main absorbent body base material to the back-side band base material and the abdominal-side band base material. Thereafter, the overlapped back-side band base material and the abdominal-side band base material are cut with a device such as that disclosed in PTL 1 to form a back-side band base material piece and an abdominal-side band base material piece. The pieces of band base materials formed and the main absorbent body base material joined to the pieces of the band base material continue to be transported in the transport direction. (See PTL 1)

CITATION LIST

Patent Literature
   [PTL 1] Japanese Patent Application Laid-open Publication No. 2008-253633

SUMMARY OF INVENTION

Technical Problem

By the way, in the final state of the band base material and the band base material piece, there exists a portion where the aforementioned protrusion is formed. The portion where this protrusion is formed is a portion that is thin and lacks rigidity compared to the portion where the band base material and the band base material piece are overlapped with the main absorbent body base material. Therefore, when the band base material piece is transported with the main absorbent body base material, the portion where the protrusion is formed to the band base material piece becomes easily twisted. When such twisting occurs, there is fear that a problem may be posed from the viewpoint of manufacturing the absorbent article.

The present invention has been made in view of the above problem and an object thereof is to prevent twisting from occurring to the back-side band base material piece and the abdominal-side band base material piece which become bases of the back-side band and the abdominal-side band.

Solution to Problem

In order to solve the above-described problem, a principal aspect of the invention is, a method for manufacturing an absorbent article including a main absorbent body having an absorbent body that absorbs liquid and that can be put against a crotch when worn, a back-side band that intersects the main absorbent, body at one longitudinal end portion of the main absorbent body, and that is positioned on a back side when worn, and an abdominal-side band that intersects the main absorbent body at another longitudinal end portion of the main absorbent body, and that is positioned on an abdominal side when worn, and has two protruding portions that protrude from both ends of the main absorbent body in a direction intersecting the longitudinal direction of the main absorbent body, formed to the back-side band and the abdominal-side band, respectively, the method including joining, during transportation of a continuous back-side band base material and a continuous abdominal-side band base material in a transport direction, one longitudinal end portion of a main absorbent body base material to the back-side band base material and another longitudinal end portion of the absorbent body base material to the abdominal-side band base material, so that the longitudinal direction of the main absorbent body base material intersects the transport direction, folding the main absorbent body base material and overlapping the back-side band base material with the abdominal-side band base material, temporarily joining the overlapped back-side band base material and abdominal-side band base material at a portion where the protruding portion is formed cutting the temporarily joined back-side band base material and abdominal-side band base material and forming a back-side band base material piece and an abdominal-side band base material piece; and transporting the back-side band base material piece, the abdominal-side band base material piece and the main absorbent body base material in the transport direction with the back-side band base material piece and the abdominal-side band base material piece in a temporarily joined state at a portion where the protruding portion is formed.

Features of the invention other than the above will become clear from the description of the present specification and the drawings attached.

Advantageous Effects of Invention

According to the present invention, twisting can be prevented from occurring to the back-side band base material piece and the abdominal-side band base material piece which become bases of the back-side band and the abdominal-side band.

BRIEF DESCRIPTION OF DRAWINGS

FIG. 4 is a diagram showing continuous body 1a.

FIG. 12 is a diagram showing the temporarily joining points in the protruding portion bases 21a and 31a.

MODE FOR CARRYING OUT THE INVENTION

Figure 1A:
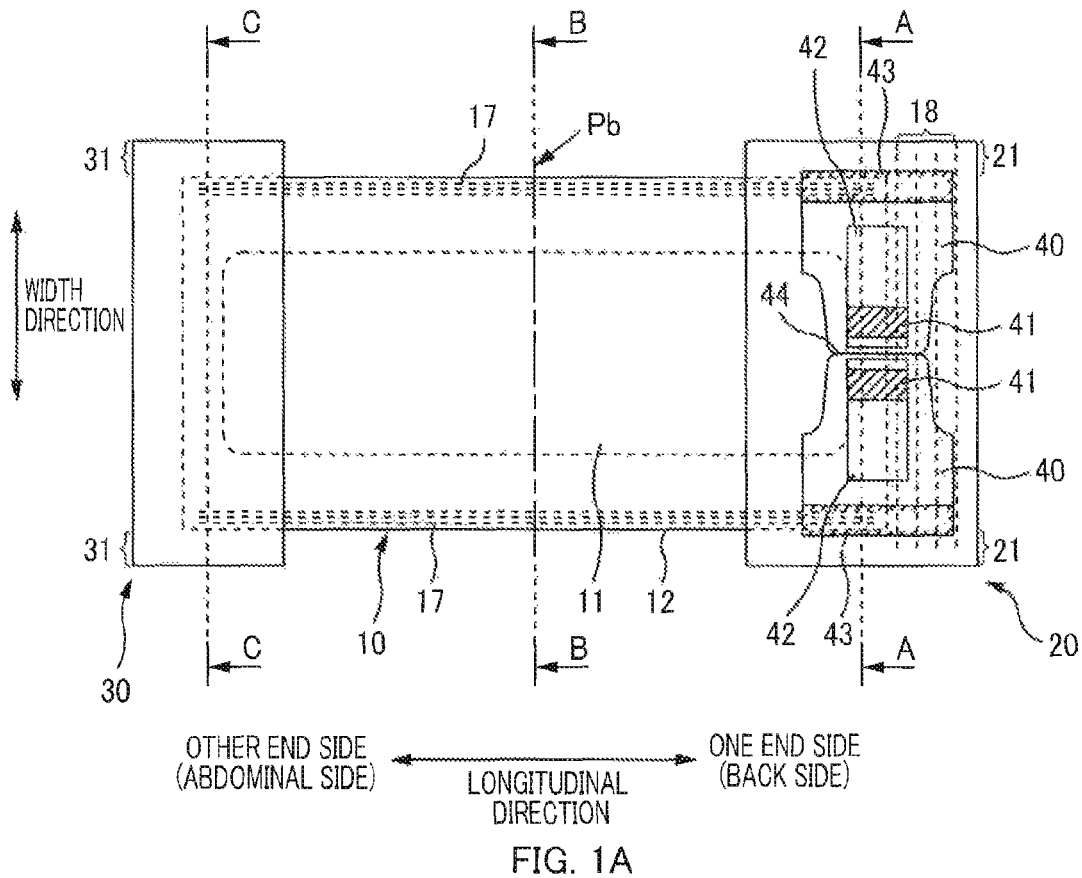
FIG. 1A is a diagram, showing diaper 1 in an unfolded state (No. 1).

At least the following matters will be made clear from the description of the present specification with reference to the accompanying drawings.

First, the method of manufacturing an absorbent article according to the present invention is a method for manufacturing an absorbent article including a main absorbent body having an absorbent body that absorbs liquid and that can be put against a crotch when worn, a back-side band that intersects the main absorbent body at one longitudinal end portion of the main absorbent body, and that is positioned on a back side when worn, and an abdominal-side band that intersects the main absorbent body at another longitudinal end portion of the main absorbent body, and that is positioned on an abdominal side when worn, and has two protruding portions that protrude from both ends of the main absorbent body in a direction intersecting the longitudinal direction of the main absorbent body, formed to the back-side band and the abdominal-side band, respectively, the method including joining, during transportation of a continuous back-side band base material and a continuous abdominal-side band base material in a transport direction, one longitudinal end portion of a main absorbent body base material to the back-side band base material and another longitudinal end portion of the absorbent body base material to the abdominal-side band base material, so that the longitudinal direction of the main absorbent body base material intersects the transport direction, folding the main absorbent body base material and overlapping the back-side band base material with the abdominal-side band base material, temporarily joining the overlapped back-side band base material and abdominal-side band base material at a portion where the protruding portion is formed, cutting the temporarily joined back-side band base material and abdominal-side band base material and forming a back-side band base material piece and an abdominal-side band base material piece, and transporting the back-side band base material piece, the abdominal-side band base material piece and the main absorbent body base material in the transport direction with the back-side band base material piece and the abdominal-side band base material piece in a temporarily joined state at a portion where the protruding portion is formed. According to this method of manufacturing an absorbent article, the two band base materials are temporarily joined at the portion where the protruding portions are formed and then cut which allows the band base material piece and the main absorbent body base material to be transported while inhibiting the above-mentioned twisting. Thereby, stable manufacturing of absorbent articles achieving desired quality is made possible.

Further according to the above method of manufacturing an absorbent article, the back-side band base material and the abdominal-side band base material are temporarily joined at at least one of the two portions where the protruding portions are formed, when temporarily joining the overlapped back-side band base material and abdominal-side band base material, and the back-side band base material piece, the abdominal-side band base material piece and the main absorbent body base material are transported with, of two portions where the two protruding portions are formed, a portion positioned on a downstream side in the transport direction where the protruding portion is formed is in a temporarily joined state, when the back-side band base material piece, the abdominal-side band base material piece and the main absorbent body base material are transported in the transport direction with the back-side band base material piece and the abdominal-side band base material piece in a state temporarily joined at a portion where the protruding portion is formed. When the band base material piece is transported with the main absorbent body base material, the portion where there is formed a protruding portion at a position on the downstream side in the transport direction is susceptible to twisting, but twisting can be effectively inhibited with the above described manufacturing method.

Further according the above method of manufacturing an absorbent article, is a method for manufacturing the absorbent article including an elastic portion that is spanned from a one end portion to another end portion in a direction intersecting the longitudinal direction of the main absorbent body, of at least one band between the back-side band and the abdominal-side band, and that imparts elasticity to the at least one band, includes joining, along the transport direction an elastic portion base material, to at least one base band material between the back-side band base material and the abdominal-side band base material, overlaps, the back-side band base material with the abdominal-side band base material, in a state where the at least one band material is joined to the elastic portion base material, when overlapping the back-side band base material with the abdominal-side band base material, temporarily joins the back-side band base material and the abdominal-side band base material so that a temporary joining point, at a portion where the protruding portion is formed, avoids a joining point of the elastic portion base material, when temporarily joining the overlapped back-side band base material and abdominal-side band base material. According to this method of manufacturing an absorbent article, the back-side band base material and the abdominal-side band base material can be temporarily joined in an appropriate manner.

Furthermore, according to the above method of manufacturing an absorbent article, the elastic portion and the elastic portion base material are composed of an elastic string, and intermittent temporary joining of the back-side band base material and the abdominal-side band base material is performed in a direction intersecting the transport direction so that a temporary joining point at a portion where the protruding portion is formed avoids a joining point of the elastic string, when temporarily joining the overlapped back-side band base material and abdominal-side band base material. According to this method of manufacturing an absorbent article, as a result of the temporary joining point at the portion where a protruding portion is formed is made to easily avoid the joining point of the elastic string, the back-side band base material and the abdominal-side band base material can be temporarily joined in a more appropriate manner.

Furthermore, according to the above method of manufacturing an absorbent article is a method for manufacturing the absorbent article including a connection piece that attaches to the protruding portion of the back-side band and connects the back-side band and the abdominal-side band when worn, may include joining a connection piece base material to a portion where the protruding portion of the back-side band base material is formed, overlap the back-side band base material with the abdominal-side band base material so that the connection piece base material is sandwiched between a portion where the protruding portion of the back-side band base material is formed and a portion where the protruding portion of the abdominal-side band base material is formed, when overlapping the back-side band base material with the abdominal-side band base material, temporarily join the back-side band base material and the abdominal-side band base material so that a temporary joining point at a portion where the protruding portion is formed avoids a point where the connection piece base material is sandwiched, when temporarily joining the overlapped back-side band base material and abdominal-side band base material. It is preferable that the thickness of the temporary joining point is thin as possible with regard to appropriate temporary joining. From such view, it is preferable that the two band base materials are temporarily joined so that the temporary joining point where a protruding portion is formed avoids the part where the connection piece base material is sandwiched. Further, when the temporary joining point becomes a point that avoids the part at which the connection piece base material is sandwiched, and when the two band base materials are temporarily joined together so that the point corresponding to the aforementioned temporary joining point does not touch the skin of the wearer when wearing the absorbent article, the quality of the absorbent article can be improved.

More further, according to the above method of manufacturing an absorbent article, a portion where the protruding portion is formed is moved in a rotation direction of a rotatable roller to a position where the back-side band base material and the abdominal-side band base material are temporarily joined, by rotating the rotatable roller having laid on the outer circumferential surface thereof the back-side band base material and the abdominal-side band base material, and the back-side band base material and the abdominal-side band base material are temporarily joined at portions where the protruding portions are formed, when temporarily joining the overlapped back-side band base material and abdominal-side band base material, and portions where the protruding portion are formed are moved in a rotation direction from the temporary joining position to a cutting position where the back-side band base material and the abdominal-side band base material are cut, by rotating the rotatable roller having laid on the outer circumferential surface thereof the back-side band base material and the abdominal-side band base material, and the back-side band base material and the abdominal-side band base material are cut at ends of portions where the protruding portions are formed, when cutting the temporarily joined back-side band base material and abdominal-side band base material. According to this method of manufacturing an absorbent article, as a result of the temporary joining position and the cutting position being positioned along the rotational direction of the rotatable roller, displacement of the temporary joining point where a protruding portion is formed and displacement of the cutting point can be suppressed.

Regarding Absorbent Articles

The method of manufacturing an absorbent article of the present invention is applied to a method for manufacturing, for example, disposable diapers (hereafter, diaper 1). The present section will explain an example of the configuration of diaper 1 and an exemplary manufacturing method of diaper 1. Note that, in the following explanation, the side that touches the body of the wearer in the thickness direction of diaper 1 will be called the skin side and the opposite side thereof, the back side, for explanatory reasons.

<<Configuration of Diaper 1>>

Figure 1B:
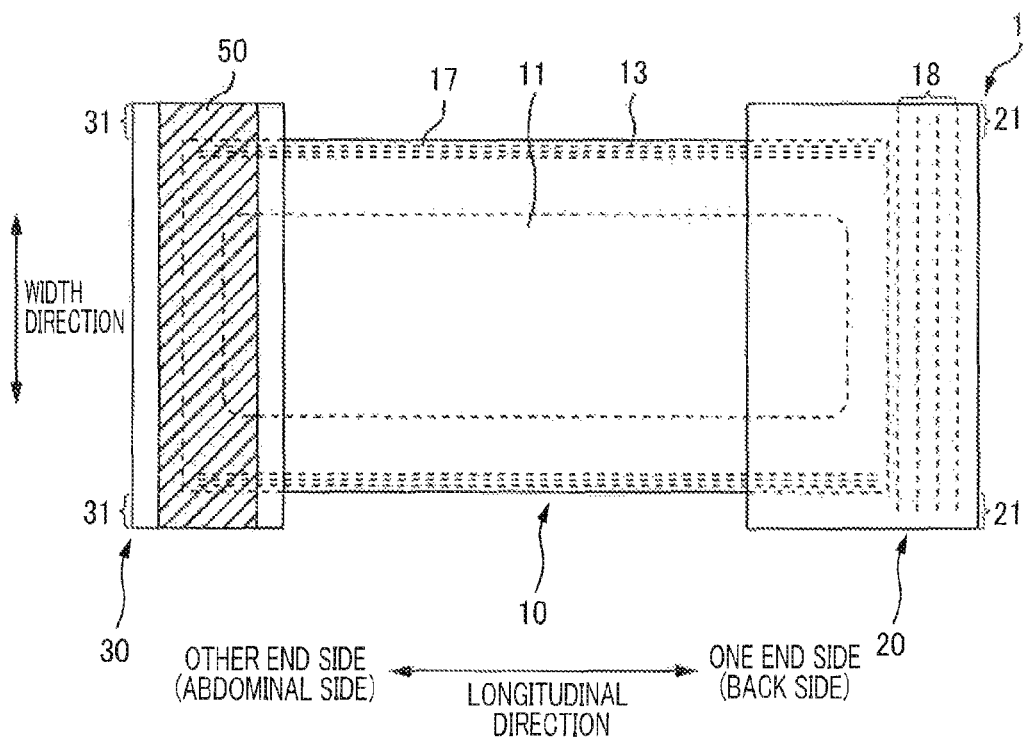
FIG. 1B is a diagram showing diaper 1 in an unfolded state (No. 2).
Figure 2A:
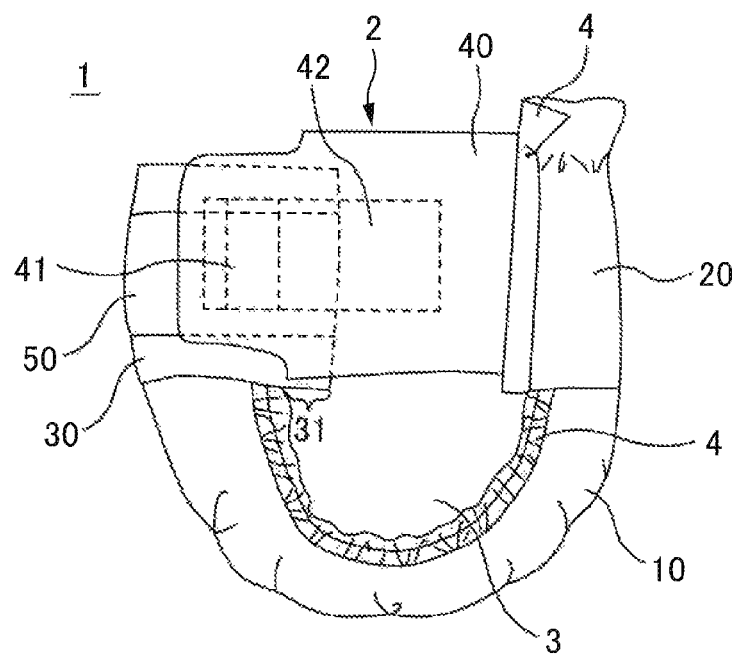
FIG. 2A is a diagram showing diaper 1 in a worn state (No. 1).
Figure 2B:
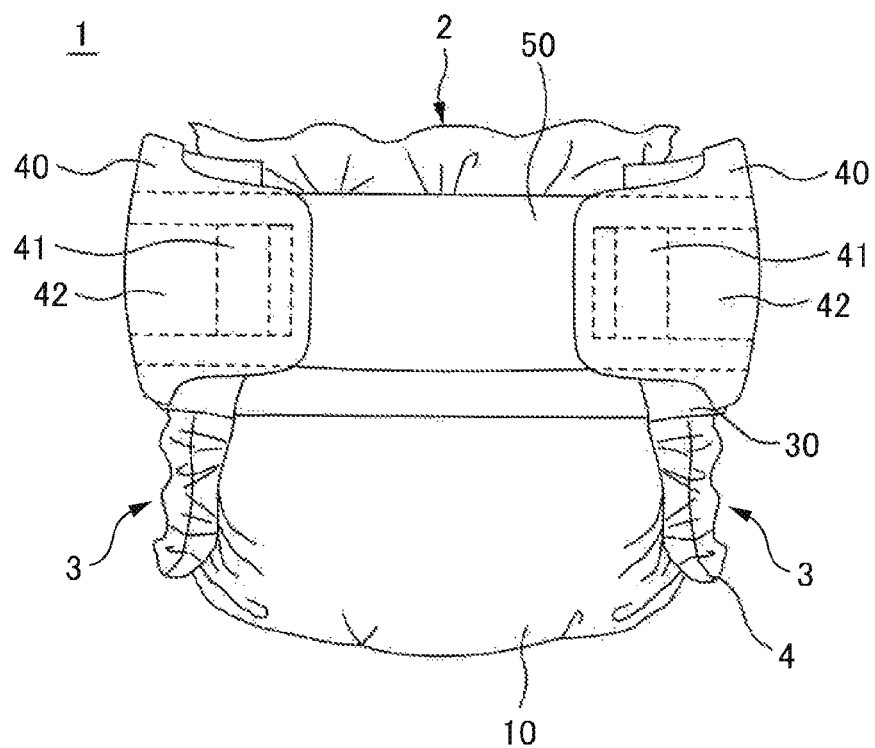
FIG. 2B is a diagram showing diaper 1 in a worn state (No. 1).
Figure 3A:
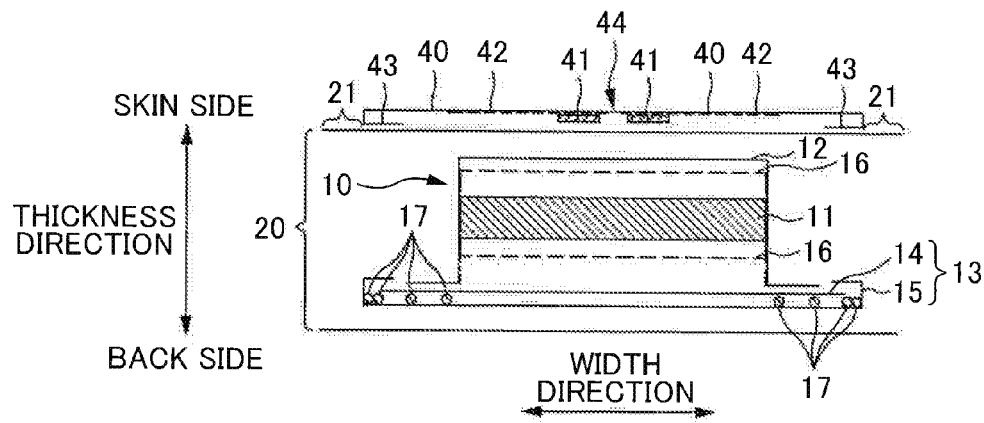
FIG. 3A is a sectional diagram taken along line A-A of FIG. 1A.
Figure 3B:
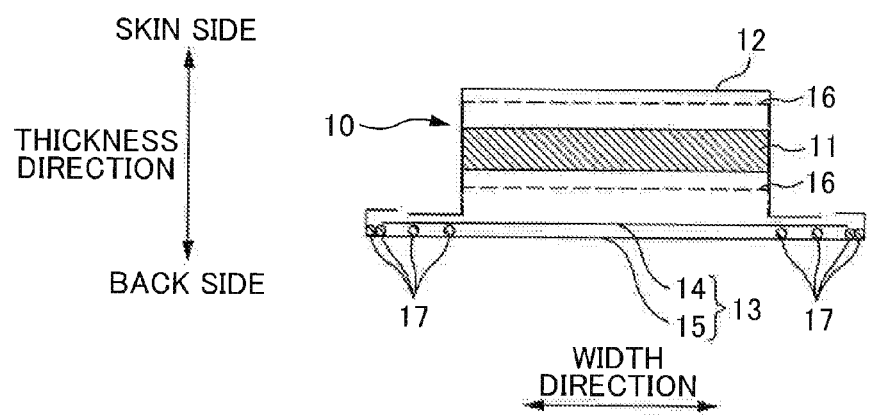
FIG. 3B is a sectional diagram taken along line B-B of FIG. 1A.
Figure 3C:
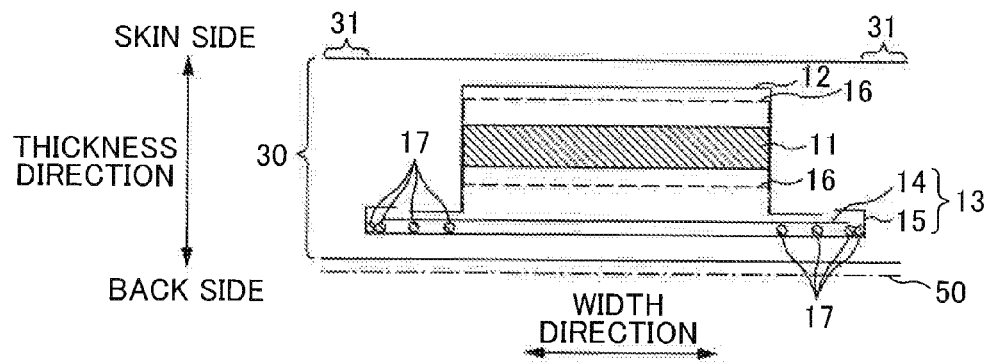
FIG. 3C is a sectional diagram taken along line C-C of FIG. 1A.

First, the configuration of diaper 1 will be explained. FIG. 1A is a view of diaper 1 in an unfolded state seen from the skin side and FIG. 1B is a view seen from the back side. FIGS. 2A and 2B are views of diaper 1 in a worn state. FIGS. 3A to 3C are sectional diagrams taken along lines A-A, B-B and C-C of FIG. 1A (FIGS. 3A and 3C show the above-mentioned sectional diagrams in a state partially exploded in the thickness direction of diaper 1). Note that, FIGS. 1A and 1B show arrows in the longitudinal direction of main absorbent body 10 and a direction that intersects the longitudinal direction (hereafter, width direction), and FIGS. 3A to 3C show the thickness direction and the width direction with arrows.

Diaper 1 is first in an unfolded state (refer to FIG. 1A) and used in a wearable folded state (refer to FIGS. 2A and 2B). Diaper 1 includes main absorbent body 10 that is set against the crotch when worn and that absorbs body fluid (corresponding to liquid) such as urine, back-side band 20 positioned on the back side of the wearer, abdominal-side band 30 that is positioned on the abdominal-side, and a connection piece 40 that connects the back-side band 20 and the abdominal-side band 30.

Figure 13:
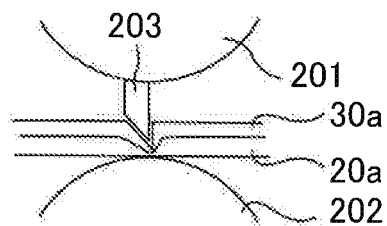
FIG. 13 is a diagram showing the way in which continuous body 1a is cut.

The appearance of diaper 1 in an unfolded state is, as shown in FIGS. 1A and 13, form an approximately H shape seen in the thickness direction where the abdominal-side band 20 and the back-side band 30 are spaced and aligned in parallel with the main absorbent body 10 spanning therebetween. From such state, the main absorbent body 10 is folded into half at the center in the longitudinal direction as the folding position Pb, and the back-side band 20 and the abdominal-side band 30 opposing each other in the bi-fold state are connected in an annular form through the connection piece 40. At this time, the connection piece 40 circles around from the back side to the abdominal side and is fixed with a detachable fastening tape 41 aside the wearer's abdomen.

Connection of the back-side band 20 and the abdominal-side band 30 allows diaper 1 to be in a wearable state as shown in FIG. 2B. In the wearable state, the back-side band 20, abdominal-side band 30 and the connection piece 40 are made to cover the waist circumference and forms a body encircling opening 2 and a pair of leg encircling openings 3 (refer to FIGS. 2A and 2B). Description on the components (main absorbent body 10, back-side band 20, abdominal-side band 30, connection piece 40 and others) of diaper 1 will follow.

The main absorbent body 10 is a rectangular layered sheet and includes an absorbent body 11 that absorbs body fluid such as urine, top sheet member 12 that covers the absorbent body 11 from the wearer's skin side, and backsheet member 13 that covers the absorbent body 11 from the side opposite the top sheet member 12 also serves as a covering of the diaper 1. The absorbent body 11 is made from absorbent fiber such as pulp fiber including superabsorbent polymer and the like. The top sheet member 12 is a liquid permeable nonwoven fabric whose two-dimensional size is larger than the absorbent body 11. The backsheet member 13 is a liquid impermeable sheet, for example, a two-layer structure having liquid impermeable leakproof sheet 14 such as polyethylene affixed to cover sheet 15 such as nonwoven fabric, whose two-dimensional size is larger than the absorbent body 11. The backsheet member 13 and the top sheet member 12 are affixed together sandwiching the absorbent body 11 therebetween, at a part sticking out to the outside from the four sides of the absorbent body 11.

Note that, as shown in FIG. 3B, between the top sheet member 12 and the absorbent body 11 or between the backsheet member 13 and the absorbent body 11, liquid permeable sheet 16 such as tissue paper can be provided. Further, at both end portions in the width direction of the backsheet member 13, a gather forming member 17 composed of an elastic string can be attached along the longitudinal direction between the leakproof sheet 14 and the cover sheet 15. In this way, elasticity is imparted to the parts around the leg encircling openings 3 of the diaper 1 to form a gather portion 4 around the legs (refer to FIGS. 2A and 2B). Note that, three-dimensional gather portions (not shown) may be provided instead of gather portion 4 around the legs.

The back-side band 20 and the abdominal-side band 30 are elements in strip form made with a soft sheet such as nonwoven fabric, and the bands 20 and 30 are configured with two overlapping sheets of nonwoven fabric. The bands 20 and 30 are respectively positioned at the longitudinal end portions of the main absorbent body 10, and intersect the main absorbent body 10. Specifically, the back-side band 20 intersects the main absorbent body 10 at one longitudinal end portion of the main absorbent body 10 and the abdominal-side band 30 intersects the other longitudinal end portion of the main absorbent body 10. Note that, as shown in FIGS. 3A and 3B, the longitudinal end portion of the main absorbent body 10 can be sandwiched between the two overlapping nonwoven fabric configuring bands 20 and 30.

A further description of the back-side band 20 and the abdominal-side band 30 will follow. Bands 20, 30 are formed in a generally rectangular form seen from the thickness direction of the bands 20, 30 and the length in the width direction (in other words, the longitudinal direction of the bands 20, 30) of the bands 20, 30 are aligned. Additionally, as shown in FIGS. 1A and 1B, both ends of the bands 20, 30 protrude out from the end of the above-described main absorbent body 10. That is, in the direction intersecting the longitudinal direction of the main absorbent body 10, two protruding portions 21, 31 protruding out from both ends of the main absorbent body 10, are formed on both the back-side band 20 and the abdominal-side band 30, respectively.

A pair of connection pieces 40 is adhered on the skin side surface of the back-side band 20 at a position rather to the center than the end in the width direction. The pair of connection pieces 40 is made of nonwoven fabric and the like and is provided symmetrically about the centerline of diaper 1. When diaper 1 is worn, each pair of the connection piece 40 is opened toward the outside from the inside when in a folded closed state. Fastening tape 41 is adhered at the end on the surface side facing the skin side at this opened state. End portions on the fixed end side 43 of the connection pieces 40 are folded back in a mountain fold state and joined to the protruding portion 21 of the back-side band 20. Note that, a stiffening sheet 42 that strengthens the rigidity around the connection piece 40 may be provided between the connection piece 40 and the fastening tape 41. Further, a pair of connection pieces 40 is connected in a one piece state at the time of shipping diaper 1 and is divided along the perforation 44 (refer to FIG. 1A) being a dividing line when wearing the diaper 1.

On the other hand, target tape 50 is adhered on the back side surface of the abdominal-side band 30. This target tape 50 is nonwoven fabric for fixing the fastening tape 41. Elastic portion 18 having elasticity may be fixed in an extended state to at least one band between back-side band 20 and abdominal-side band 30 to impart elasticity to at least one of the bands. For example, as shown in FIG. 1A, an elastic portion composed of an elastic string is fixed to the back-side band 30 and elasticity may be imparted to the back-side band 30. As shown in the drawing, it is preferable that the elastic portion 18 is spanned from one end to the other end of the back-side band 20 in the width direction and a plurality of them are provided at predetermined intervals in the longitudinal direction.

<<Example of Manufacturing Method of Diaper 1>>

Next, an example of a manufacturing method of diaper 1 will be explained.

Figure 4:
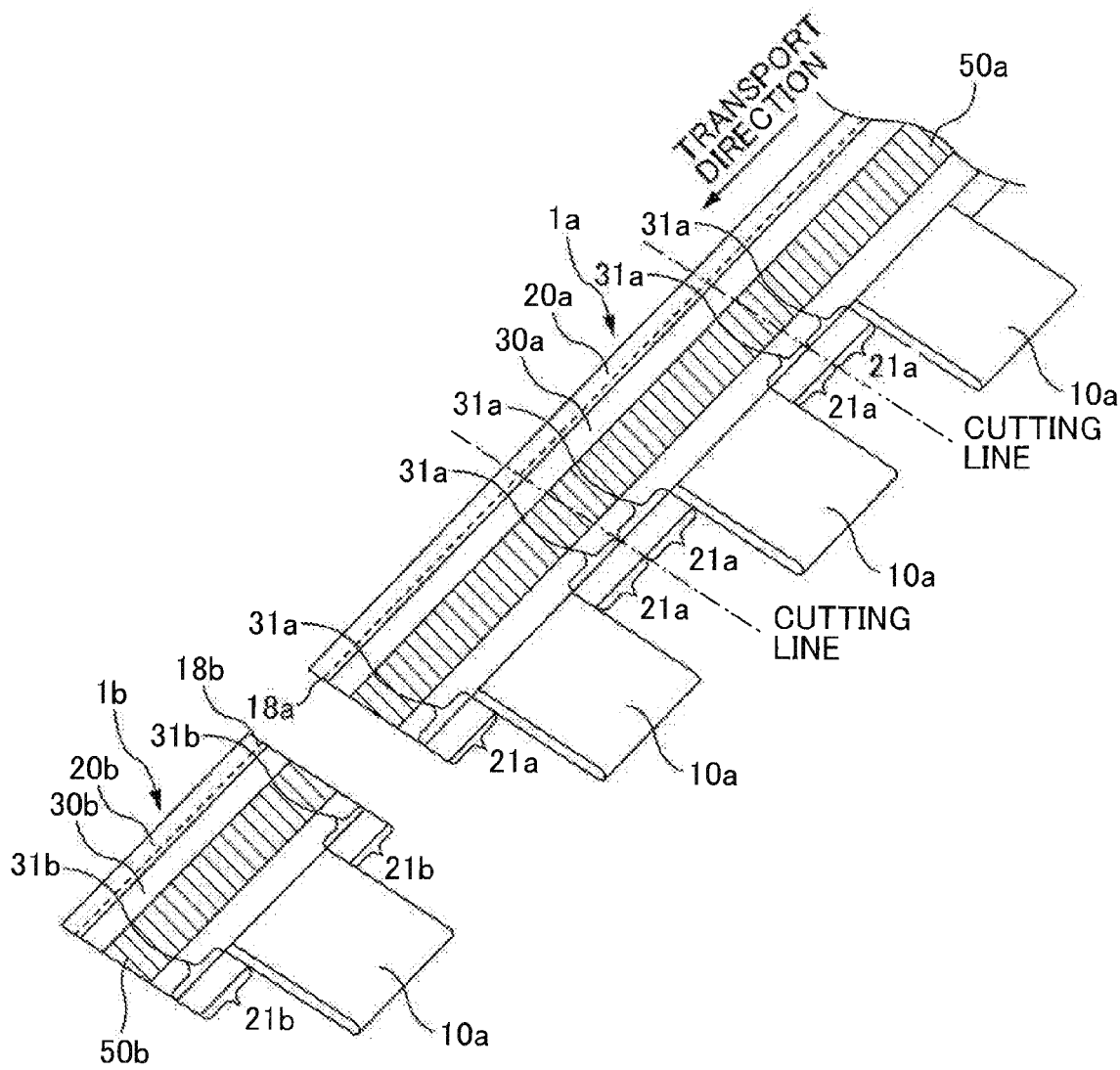

Diaper 1 is continuously manufactured in a continuous manufacturing line. In this continuous manufacturing line, continuous body 1a is formed by transporting base materials that form diaper 1 in the transport direction while joining the base materials together, as shown in FIG. 4. FIG. 4 is a diagram showing the continuous body 1a. The continuous body 1a is continuous along the transport direction. And when the continuous body 1a is cut in product units along tine transport direction, diaper 1 as a final, product is completed. Explanation on the flow for forming the continuous body 1a will follow.

When the continuous body 1a is formed, first, the back-side band base material 20a and the abdominal-side band base material 30a continuous in a belt form are transported in the transport direction. The band base materials 20a, 30a are original fabrics of the back-side band 20 or the abdominal-side band 30, respectively and are unrolled from a rolled state to be transported along the continuous direction thereof. Note that the band base materials 20a, 30a are transported in a state spaced and aligned approximately parallel (refer to FIG. 5).

Figure 5:
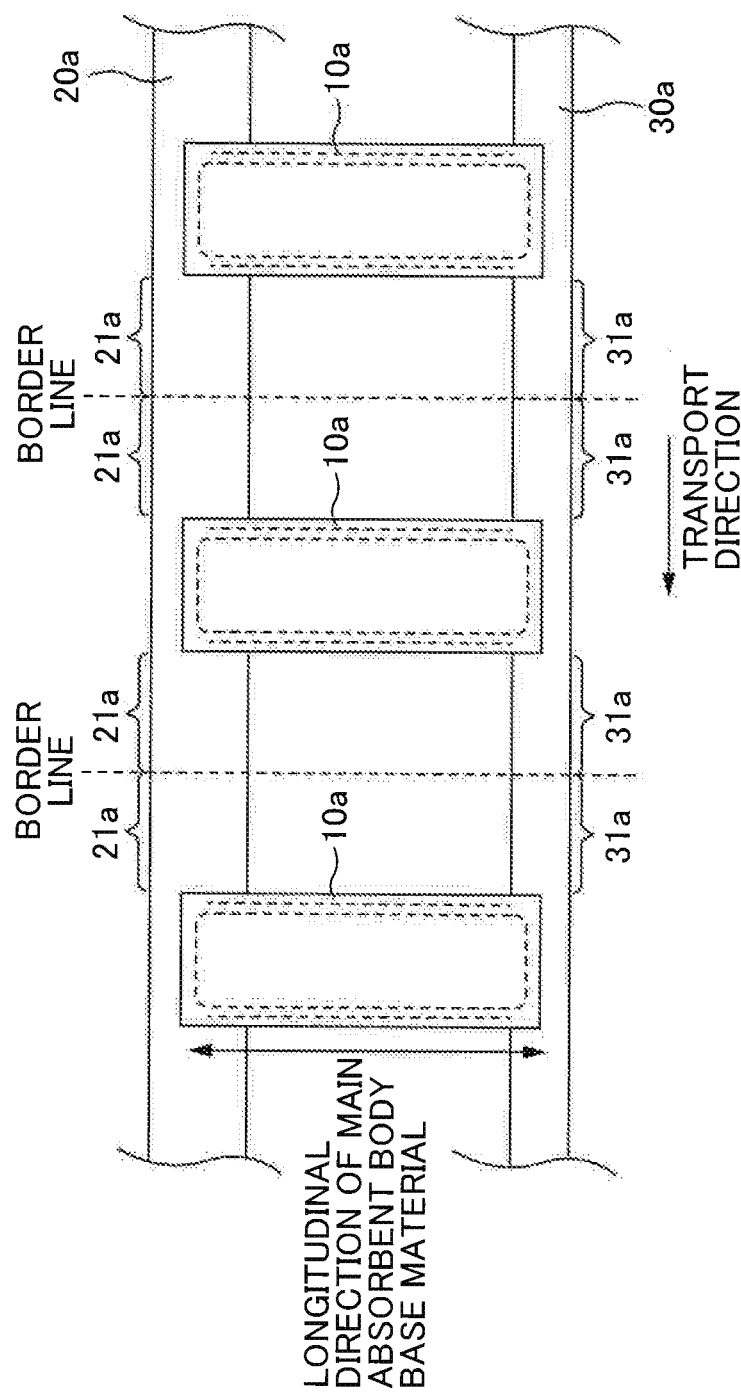
FIG. 5 is a diagram showing band base materials 20a and 30a, and the main absorbent body base material spanning across the band base materials 20a and 30a during transport.

As shown in FIG. 5, while the band base materials 20a, 30a are transported, main absorbent body base material 10a is spanned across the band base materials 20a, 30a and joined thereto at a predetermined interval along the transport direction. FIG. 5 is a diagram showing the band base materials 20a, 30a being transported with the main absorbent body base material 10a spanned across the band base materials 20a, 30a. Note that the main absorbent body base material 10a is a material that becomes the base of the main absorbent body 10 and through the processes of the continuous manufacturing line of diaper 1, becomes the main absorbent body 10 in the end.

As described above, while the back-side band base material 20a and the abdominal-side band base material 30a are transported in the transport direction, one longitudinal end portion of the main absorbent body base material 10a is joined to the back-side band base material 20a and the other longitudinal end portion of the main absorbent body base material 10a is joined to the abdominal-side band base material 30a so that the longitudinal direction of the main absorbent body base material 10a and the transport direction intersect. As the joining method, a preferable joining method for joining the main absorbent body base material 10a with the band base materials 20a, 30a may be selected from well known joining methods.

Figures 6A, 6B, 6C:
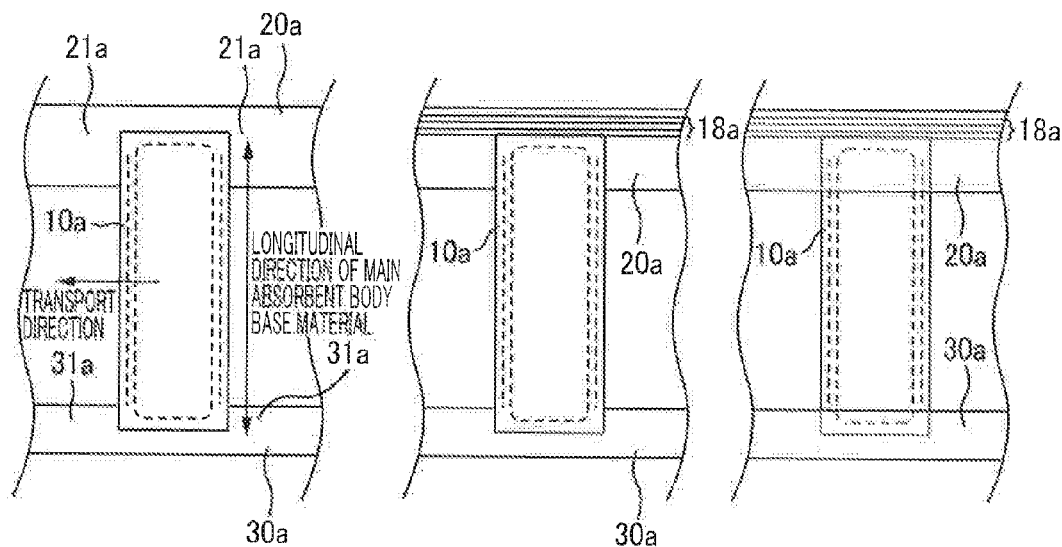
FIG. 6A is a transition diagram showing the forming process of continuous body 1a (No. 1).
FIG. 6B is a transition diagram showing the forming process of continuous body 1a (No. 2).
FIG. 6C is a transition diagram showing the forming process of continuous body 1a (No. 3).

When manufacturing diaper 1 using two layered nonwoven fabric for the bands 20, 30 and having the longitudinal end portion of the main absorbent body 10 sandwiched between the aforementioned two layered nonwoven fabric, the main absorbent body base material 10a can be joined to one of the nonwoven fabric while this nonwoven fabric is transported and thereafter, the other nonwoven fabric can be overlapped on and attached to the one of the nonwoven fabric (refer to FIGS. 6A and 6C).

With the above procedures, portions 21a, 31a where the above-mentioned protrusions 21, 31 are formed in the future (when diaper 1 is completed) at a portion of band base materials 20a, 30a located between main absorbent body base materials 10a. As shown in FIG. 5, these portions 21a, 31a (hereafter, protruding portion base) are formed on both sides of the main absorbent body base materials 10a at band base materials 20a, 30a. In other words, there are two protrusion bases 21a, 31a for a single main absorbent body base material 10a. Further, as shown in FIG. 5, a pair of protrusion bases 21a, 31a is formed adjacent to each other between main absorbent body base materials 10a.

Thereafter, the main absorbent body base material 10a is transported in a state where the longitudinal direction thereof intersects the transport direction, together with band base materials 20a, 30a. Hereafter, through the states shown in FIGS. 6A and 6F, continuous body 1a is formed. FIG. 6A through FIG. 6E are transition diagrams showing the forming process of continuous body 1a.

To be specific, when elastic portion 18 is provided to at least one of bands 20, 30 between the back-side band 20 and the abdominal-side band 30, in the state shown in FIG. 6A (in a state where the main absorbent body base material 10a is joined to band base materials 20a, 30a), elastic portion base material 18a composed of an elastic string is joined, in the transport direction, to at least one of band base materials 20a, 30a of the back-side band base material 20a and the abdominal-side band base material 30a (refer to FIG. 6B). Note that elastic portion base material 18a is material to be the base of elastic portion 18 and is cut into a predetermined length to form elastic portion 18 in the end.

Figures 6D, 6E:
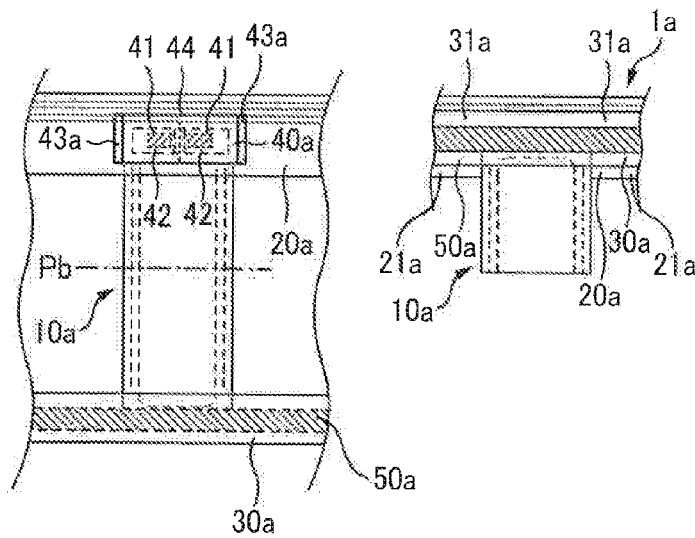
FIG. 6D is a transition diagram showing the forming process of continuous body 1a (No. 4).
FIG. 6E is a transition diagram showing the forming process of continuous body 1a (No. 5).

Thereafter, as shown in FIG. 6D, connection piece base material 40a is joined to the skin side surface of the back-side band base material 20a. The connection piece base material 40a is material to be the base of the pair of connection pieces 40 and is nonwoven fabric in a single sheet form to which perforation 44 being a dividing line is formed. When the connection piece base material 40a is joined to the back-side band base material 20a, the above-mentioned connection piece base material 40a has fastening tape 41 and stiffening sheet 42 attached to predetermined locations in advance with both ends thereof folded back. This fold back portion 43a being attached to the protruding portion base 21a of the back-side band base material 20a allows the connection piece base material 40a to be joined to back-side band base material 20a.

On the other hand, as shown in FIG. 6D, target tape base material 50a is joined to the back side surface of abdominal-side band base material 30a. The target tape base material 50a is material, to be the base of target tape 50 and is cut into a predetermined length to form target tape 50 in the end.

Thereafter, the main absorbent body 10 is folded in half at approximately the center in the longitudinal direction as the folding position Pb (refer to FIG. 6D) and the abdominal-side band base material 30a is overlapped on the back-side band base material 20a. As a result, as shown in FIG. 6E, the main absorbent body base material 10a folded in half and the overlapped band base materials form a T shape seen from above. Note that, when the band base materials 20a, 30a are overlapped, the protruding portion bases 21a, 31a of the band base materials 20a, 30a are also overlapped. Further, when the band base materials 20a, 30a are overlapped, the above described band base materials 20a, 30a are overlapped such that the connection piece base material 40a is sandwiched between the protruding portion base 21a of the back-side band base material 20a and the protruding portion base 31a of the abdominal-side band base material 30a.

Continuous body 1a is formed as a result of the processes above being repetitively performed. The continuous body 1a is cut at approximately the center location of the main absorbent body base material 10a. This location is the location of the border line between protruding portion bases 21a, 31a of band base materials 20a, 30a (border line between the adjacent pair of protruding portion bases 21a, 21a (31a, 31a) between the main absorbent body base materials 10a). That is, the band base materials 20a, 30a are cut at the ends of the protruding portion bases 21a, 31a in the transport direction.

By the cutting process, continuous body pieces 1b in an approximately product form are formed from the tail end (downstream side end in the transport direction) of the continuous body 1a. That is, back-side band base material piece 20b is formed from the back-side band base material 20a, the abdominal-side band base material piece 30b is formed from the abdominal-side band base material 30a, the elastic portion base material piece 18b is formed from the elastic portion base material 18a, and the target tape base material piece 50b is made from the target tape base material 50a (refer to FIG. 4). Each of the base material pieces 20b, 30b, 18b, and 50b were obtained by cutting each of the base materials 20a, 30a, 18a, and 50a to conform to the product shape.

Then the above continuous body piece 1a is continuously transported in the transport direction toward the following process. Thereafter, diaper 1 is completed as a product from the continuous body piece 1a to be packed and shipped in the end.

Note that, the reason for performing the cutting process sifter folding the main absorbent body base material 10 and overlapping band base materials 20a, 30a as in this example, is because if the band base materials 20a, 30a were overlapped after cutting the band base materials 20a, 30a, overlapping would be performed while holding the band base materials 20a, 30a after cutting making the operation for forming the above mentioned continuous body piece 1b complicated, but with the procedure of this example, continuous body pieces 1b can be formed more effectively. Further, if the band base materials 20a, 30a are cut after overlapping the band base materials 20a, 30a, the two band base materials 20a, 30a is cut at one time allowing to minimize the number and the size of the blades for cutting.

===Regarding Twisting of Band Base Material Pieces 20b, 30b===

With the method of producing diaper 1 according to the above example, a process is performed by cutting the band base materials 20a, 30a and forming the band base material pieces 20b, 30b and thereafter the band base material pieces 20a, 30a are continuously transported together with other base materials such as the main absorbent body base material 10a. Here protruding portion bases 21b, 31b are provided to the end portions in the transport direction of the band base material pieces 20b, 30b. The protruding portion bases 21b, 31b having low rigidity compared to the portions, of the band base material pieces 20b, 30b, overlapping with the main absorbent body base material 10a are more likely to be twisted.

Figure 7:
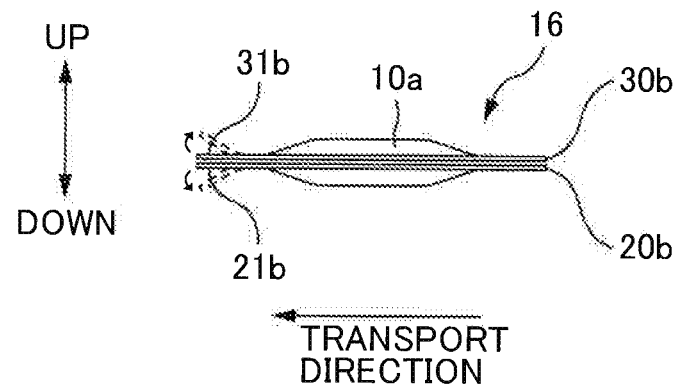
FIG. 7 is a diagram showing the twisted condition of the band base material pieces 20b and 30b at protruding portion bases 21b and 31b.

With the above described characteristic, the band base material pieces 20b, 30b would be twisted (so called, mouth opening phenomenon) at the protruding portion bases 21b, 31b while transporting the band base material pieces 20b, 30b, as shown in FIG. 7. FIG. 7 is a diagram showing the condition of the twisted band base material pieces 20b, 30b and is a diagram of the continuous body piece 1b during transport seen from the side of the band, base material piece 20b, 30b. Problems caused due to twisting of the band base material pieces 20b, 30b is explained in the following with reference to FIG. 8.

Figure 8:
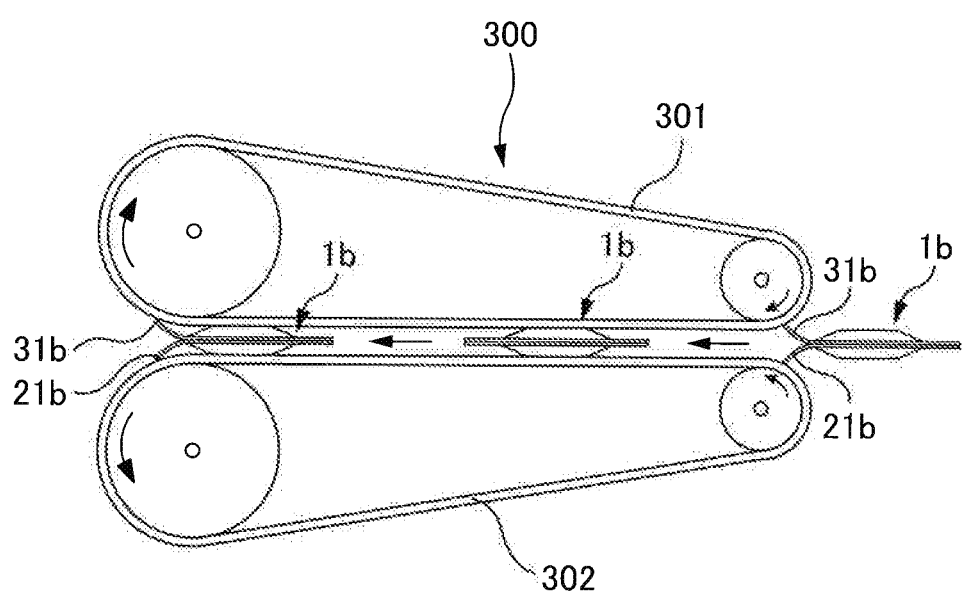
FIG. 8 is an explanatory diagram of malfunction caused by twisting.

The continuous body piece 1b is transported by, for example, a transporting device 300 as shown in FIG. 8. This transporting device 300 includes a pair of belt conveyors 301, 302 positioned and aligned one over the other and between these belt conveyors 301, 302, continuous body piece 1b is transported in a state where the entire continuous body piece 1b including the band base material pieces 21b, 31b is sandwiched. When the band base material pieces 21b, 31b is twisted at the end portion in the transport direction (particularly, the end portion on the downstream side in the transport direction), it would be difficult for the continuous body piece 1b to enter between the belt conveyors 301, 302 when continuous body piece 1b proceeds between the belt conveyors 301, 302, making transportation of the continuous body piece 1b difficult.

Additionally, the end portion on the downstream side in the transport direction of the band base material pieces 21b, 301b would be dragged by the belt conveyors 301, 302 when the continuous body piece 1b comes out from between the belt conveyors 301, 302 so that the band base material pieces 21, 31b is more likely to be twisted. Thereafter the continuous body piece 1b comes out from between the belt conveyors 301, 302 to be diapers 1 as products and aligned for packing however, if the above twisting remains, it would be difficult to appropriately align the diapers 1. Further, in a case a predetermined process is to be performed on the continuous body piece 1b that has come out from between the belt conveyors 301, 302, it would be difficult to perform this process with the above twisting remaining.

As described above, problems due to the above twisting would effect the quality of draper 1 as a product and thus the present embodiment has taken measures for preventing the occurrence of twisting of band base material pieces 20b, 30b. The next section explains the method of producing diaper 1 of the present embodiment.

===Method of Manufacturing Diaper 1 of the Present Embodiment===

Figure 9:
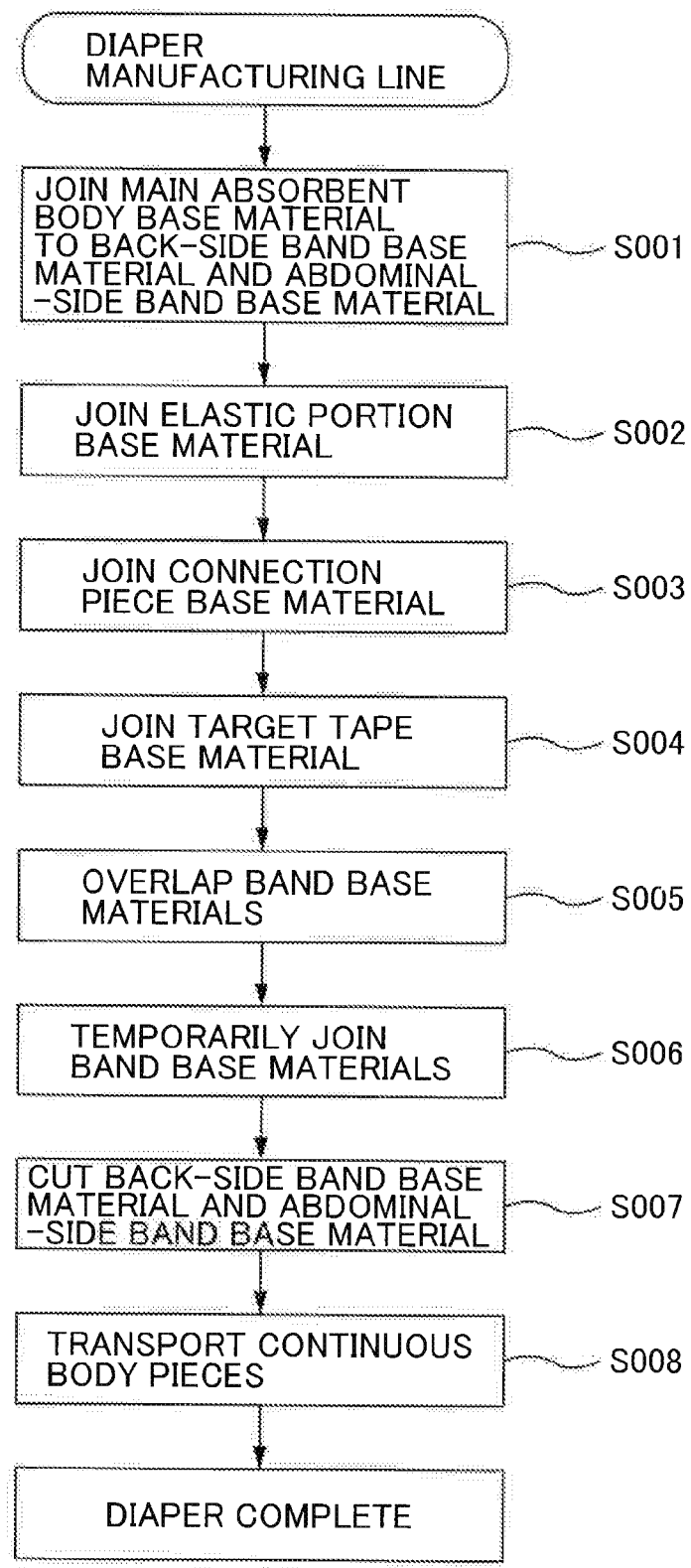
FIG. 9 is a diagram showing the processes performed at the manufacturing line of diaper 1.

The manufacturing line (manufacturing method) of diaper 1 of the present embodiment is configured by the processes shown in FIG. 9. FIG. 9 is a diagram showing the processes in the manufacturing line of diaper 1 of the present embodiment.

Specifically, the above-described manufacturing line includes, during transporting the back-side band base material 20a and the abdominal-side band base material 30a in the transport direction, a process (S001) of joining the one longitudinal end portion of the main, absorbent body base material 10a to the back-side band base material 20a, and joining the other longitudinal end portion of the main absorbent body base material 10a to the abdominal-side band base material 30a so that the longitudinal direction of the main absorbent body base material 10a intersects the transport direction, a process (S003) of joining the connection piece base material 40a to the protruding portion base 21a of the back-side band, base material 20a, and a process (S005) of folding the main absorbent body base material 10a and overlapping the back-side band base material 20a with the abdominal-side band base material 30a.

The above described processes are repetitively performed by the aforementioned procedures and thereby the continuous body 1a continuous in the transport direction is formed. Note that in the process (S005) overlapping the band base materials 20a, 30a together, the back-side band base material 20a and the abdominal-side band base material 30a are overlapped so that the connection piece base material 40a is sandwiched between the protruding portion base 21a of the back-side band base material 20a and the protruding portion base 31a of the abdominal-side band base material 30a.

At the above described manufacturing line, there is produced diaper 1 provided with elastic portion 18 spanning from one end portion to the other end portion in the width direction of at least one of the bands (back-side band 20 in the present embodiment) between the back-side band 20 and the abdominal-side band 30. Therefore the above described manufacturing line would include a process (S002) of joining in the transport direction the elastic portion base material 18a to at least one of the band base materials (the back-side band 20 in the present embodiment) between the back-side band base material 20a and the abdominal-side band base material 30a. This process is also performed by the aforementioned procedure. Note that in the process (S005) of overlapping the band base materials 20a, 30a together, the back-side band base material 20a and the abdominal-side band base material 30a are overlapped in a state where the elastic portion base material 18a is joined to at least one of the band base materials 20a, 30a.

Further, the above described manufacturing line includes a process (S004) of joining the target tape base material 50a to the back side surface of the abdominal-side band base material 30a, and sit the process (S005) of overlapping the band base materials 20a, 30a together, the band base materials 20a, 30a are overlapped in a state where the target tape base material 50a is joined to the abdominal-side band base material 30a. However, the target tape base material 50a can be joined to the abdominal-side band base material 30a after the band base materials 20a, 30a are overlapped.

In the present embodiment, after the band base materials 20a, 30a are overlapped (that is, after the continuous body 1a is formed), the band base materials 20a, 30a are temporarily joined together at the protruding portions 21a, 31a and then the continuous body 1a is cut to form continuous body pieces 1b. Thereafter with the band base material pieces 20b, 30b in a temporarily joined state, the continuous body pieces 1b are transported in the transport direction. That is, the above described manufacturing line includes a process (S006) of temporarily joining the overlapped back-side band base material 20a and the abdominal-side band base material 30a at the protruding portion bases 21a, 31a and a process (S007) of cutting the temporarily joined back-side band base material 20a and the abdominal-side band base material 30a and forming the back-side band base material piece 20b and the abdominal-side band base material piece 30b, and a process (S008) of transporting in the transport direction the continuous body piece 1b including such as the back-side band base material piece 20b, the abdominal-side band base material piece 30b, the main absorbent body base material piece 10b in a state where the back-side band base material piece 20b and the abdominal-side band base material piece 30b are temporarily joined at the protruding portion bases 21a, 31b.

In the following, among the above-described processes (S001-S008), description will be given on the temporary joining process (S006) that temporarily joins the overlapped band base materials 20a, 30a, the cutting process (S007) that cuts the temporarily joined band base materials 20a, 30a, and the transportation process (S008) that transports the continuous body piece 1b in a state where the band base materials 20a, 30a are temporarily joined.

<<Temporary Joining Process S006>>

Figure 10:
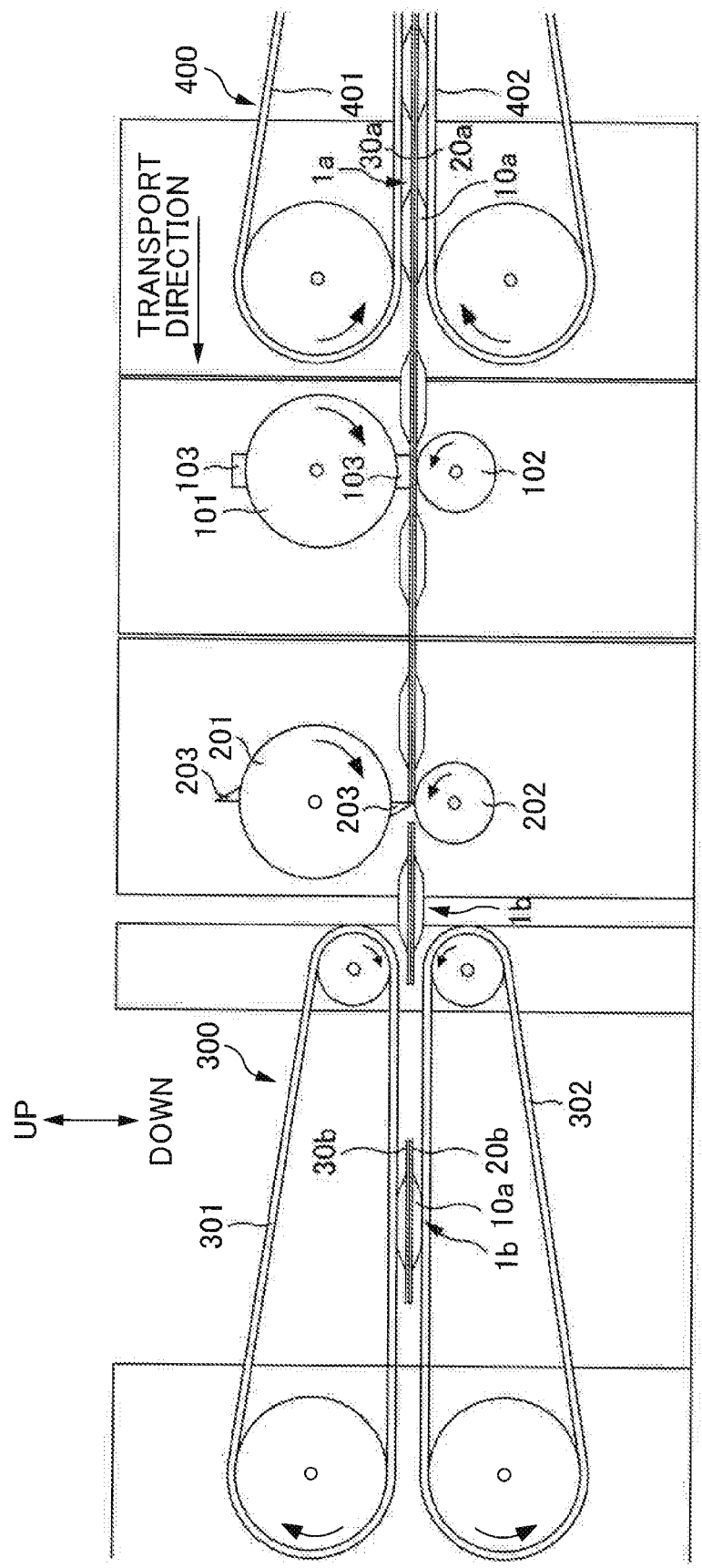
FIG. 10 is a diagram showing a part of the group of devices in the manufacturing line of diaper 1.

The present process is carried out by the device for temporary joining 100 shown in FIG. 10. FIG. 10 is a diagram showing a part of the group of devices in the diaper 1 manufacturing line. The device for temporary joining 100 sandwiches the continuous body 1a between a pair of belt conveyors 401, 402 one positioned over the other, receives the continuous body 1a from the upstream side transportation device 400 that transports the continuous body 1a, and temporarily joins the overlapped band base materials 20a, 30a of the continuous body 1a. Here, temporarily joining is joining on the premise that the band base materials 20a, 30a (or the band base material pieces 20b, 30b, bands 20, 30) are to be used in a state separated once again which means that they are joined at a level that they can be easily separated without losing their function (later capabilities as bands 20, 30) at the time of use. Note that, it is preferable that the joining strength by temporary joining is in the range of 3-5 N/cm2.

As shown in FIG. 10, the device for temporary joining 100 includes a pair of rollers for temporary joining 101, 102 one positioned over the other and rotatably supported about axes approximately perpendicular to the transport direction. The continuous body 1a moves in the transport direction so that the overlapped band base materials 20a, 30a travels through the pair of rollers for temporary joining 101, 102. Meanwhile, the device for temporary joining 100 temporarily joins the band base materials 20a, 30a together at the protruding portion bases 21a, 31a.

Note that in the present embodiment, the continuous body 1a that has come out from between the belt conveyors 401, 402 travels straight forward in the transport direction while maintaining a height allowing advancement between the rollers for temporary joining 101, 102. However, the continuous body 1a that has come out of the belt conveyors 401, 402 can be once laid on the outer circumferential surface of the lower roller for temporary joining 102 and then guided between the rollers for temporary joining 101, 102 by the rotation of the roller for temporary joining 102.

Figure 11:
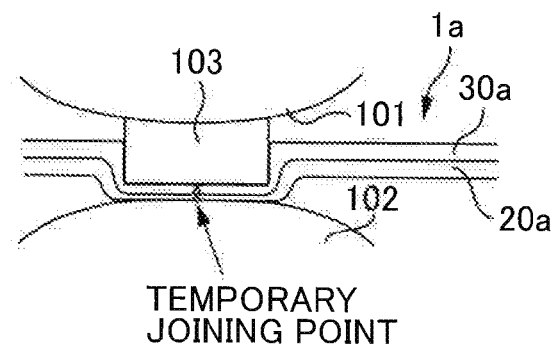
FIG. 11 is a diagram showing the way in winch the band base materials 20a and 30a are temporarily joined.

The details of the structure of the rollers for temporary joining 101, 102 are that lumps 103 are provided, on the outer circumference of the upper roller for temporary joining 101, at predetermined intervals along the circumferential direction (refer to FIG. 10). As shown in FIG. 11, each of the lumps 103 sandwiches the band base materials 20a, 30a with the outer circumferential surface of the lower roller for temporary joining 102, and embosses the sandwiched part. Embossing is a process that forms embosses by pressing while heating the overlapped band base materials 20a, 30a, and the overlapped band base materials 20a, 30a are temporarily joined at the parts where embosses are formed. FIG. 11 is a diagram showing the manner in which the band base materials 20a, 30a are temporarily joined. Note that the circumferential surface of the lower roller for temporary joining 102 can also have a lump provided to apply embossing, by sandwiching the band base materials 20a, 30a in cooperation with the lump 103 of the upper roller for temporary joining 102.

Embossing is provided at the points where the protruding portion bases 21a, 31a of the band base materials 20a, 30a overlap. That is, the band base materials 20a, 30a are temporarily joined together at the protruding portion bases 21a, 31a. Here, there are two protruding potion bases being protruding portion bases 21a of the back-side band base material 20a and protruding portion bases 31a of the abdominal-side band base material 30a provided to each main absorbent body base material 10a (refer to FIG. 4) however, in the present embodiment, the back-side band base material 20a and the abdominal-side band base material 30a are temporarily joined at at least one of the two protruding portion bases 21a, 31a. Particularly in the present embodiment, the band base materials 20a, 30a are temporarily joined together at only the latter of the protruding portion bases 21a, 31a immediately before (upstream side in the transport direction) the main absorbent body base material 10a, and the protruding portion bases 21a, 31a immediately after (downstream side in the transport direction) the main absorbent body base material 10a, seen from this main absorbent body base material.

Figure 12:
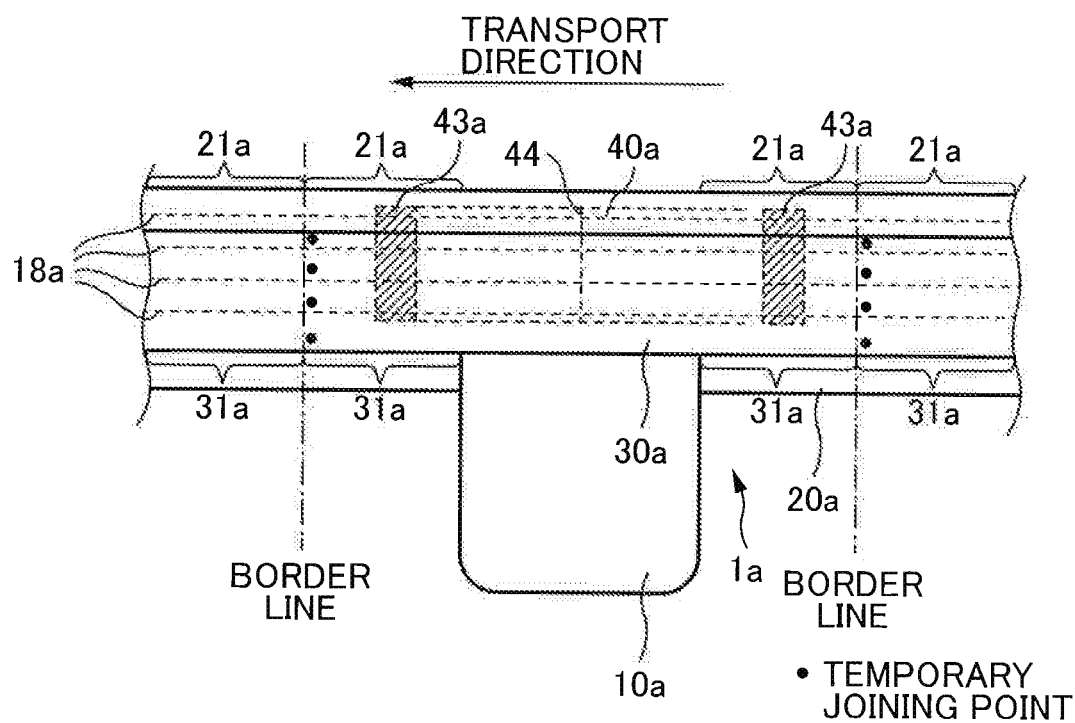

The protruding portion bases 21a, 31a can be divided into an area that has the connection piece base material 40a sandwiched between the protruding portion, bases 21a, 31a and an area that does not have the connection piece base material 40a sandwiched therebetween. As a matter of course, the latter is thinner (in other words of low-basis-weight) than the former. Here, when the overlapped band base materials 20a, 30a are temporarily joined at the protruding portion bases 21a, 31a, the thinner the temporary joining part is, the more effective temporary joining can be carried out. Therefore, during the process of temporarily joining the overlapped back-side band base material 20a and abdominal-side band base material 30a, the back-side band base material 20a and the abdominal-side band base material 30a are temporarily joined so that the temporary joining point at the protruding portion bases 21a, 31a avoids the point where the connection piece base material 40a is sandwiched, as shown in FIG. 12. FIG. 12 is a diagram showing the temporary joining point at the protruding portion bases 21a, 31a.

As shown in FIG. 12, the back-side band base material 20a and the abdominal-side band base material 30a are temporarily joined so that the temporary joining point at the protruding portion bases 21a, 31a avoids the elastic portion base material 18a in the present embodiment. If the temporary joining point comes to the joining point at the elastic portion base material 18a, the above band base materials 20a, 30a may not be appropriately temporarily joined together however, since the temporary joining is carried out avoiding the elastic portion base material 18a in the present embodiment, the band base materials 20a, 30a can be temporarily joined together appropriately.

As shown in FIG. 12, the band base materials 20a, 30a are temporarily joined together so that embossing is intermittently formed in the direction intersecting the transport direction. That is, in the present embodiment, the back-side band base material 20a and the abdominal-side band base material 30a are temporarily joined in an intermittent manner (in dots in the present embodiment) in the direction intersecting the transport direction such that the temporary joining point avoids the joining point of the elastic string configuring the elastic portion base material 18a. In this way, the temporary joining point can easily avoid the joining point of the elastic string and as a result allows the band base materials 20a, 30a to be temporary joined together more appropriately.

Note that in the present embodiment, temporary joining is carried out at predetermined intervals from one end to the other end in the direction that approximately intersects the transport direction at the end portion (end portion at the downstream side in the transport direction) of the part where the protruding portion bases 21a, 31a are overlapped, as shown in FIG. 12. In this way, a temporary joined state can be easily maintained in the processes hereafter. However, temporary joining is to be carried out at least at the end, of the part where the protruding portion bases 21a, 31a are overlapped, in the direction that approximately intersects the transport direction.

<<Cutting Process (S007)>>

This process is carried out by the cutting device 200 shown in FIG. 10. The cutting device 200 receives the continuous body 1a from the device for temporary joining 100 and cuts the back-side band base material 20a and the abdominal-side band base material 30a along the previously discussed cutting line (refer to FIG. 4). In this way approximately product shaped continuous body pieces 1b are formed from the continuous body 1a.

As shown in FIG. 10, the cutting device 200 includes a pair of cutting rollers 201, 202 one positioned over the other and rotatably supported about axes approximately perpendicular to the transport direction. The continuous body 1a moves in the transport direction, so that the temporarily joined band base materials 20a, 30a travels between the pair of cutting rollers 201, 202. Meanwhile, the cutting device 200 cuts the continuous body 1a along the cutting line.

The details of the cutting rollers 201, 202 are that the upper cutting roller 201 is a so-called cutter-roller and has an approximately wedge shaped blade 203 on the outer circumference thereof, as shown in FIG. 10. As shown in FIG. 13, this blade 203 sandwiches the temporarily joined band base materials 20a, 30a in cooperation with the outer circumferential surface of the lower cutting roller 202 at a point where the above-described cutting line is located. In this way, the continuous body 1a is cut along the cutting line to form continuous body pieces 1b. FIG. 13 is a diagram showing the way in which the continuous body 1a is cut.

Note that, cutting lines are provided at predetermined intervals along the transport direction and the number of blades 203 provided is that enough for sandwiching with the outer circumferential surface of the lower cutting roller 202, the point at which the cutting lines of the continuous body 1a are located. Additionally, for example, a lump-shaped blade receiving portion for receiving the above-described blade 203 can be provided to the outer circumference of the lower roller for temporary joining 102 and this blade receiving portion and the blade 203 can sandwich the band base materials 20a, 30a to cut the continuous body 1a.

By the way, the cutting line corresponds to the border line between the pair of protruding portion bases 21a, 21a (31a, 31a) between those adjacent to each other between the main absorbent body base materials 10a so by cutting the continuous body 1a along the cutting line, the pair of protruding portion bases 21a, 21a (31a, 31a) that, were adjacent are cut apart. As a result, band base materials 20a, 30a are cut in pieces at the downstream side along the transport direction to form band base material pieces 20b, 30b.

Figure 14:
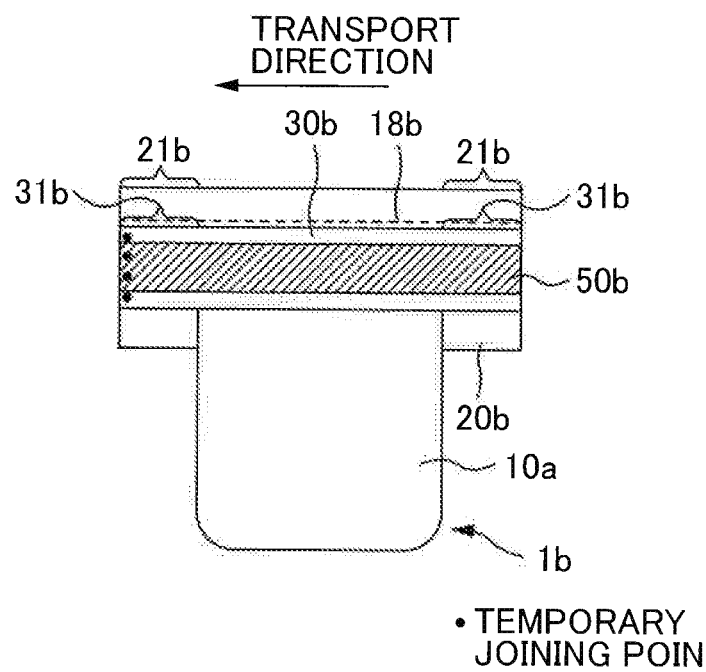
FIG. 14 is a planar diagram of the continuous body piece 1b.

In the present embodiment, since the band base materials 20a, 30a are temporarily joined together only at the protruding portion bases 21a, 31a immediately following (downstream side along the transport direction) the main absorbent body base material 10a, when the continuous body 1a is cut along the cutting line, a temporary joined state is maintained at the side of the temporarily joined protruding portion bases 21b, 31b. However, the side of the protruding portion bases 21a, 31a at which temporary joining is not performed, is in a state where the band base material pieces 20b, 30b are merely overlapped (not joined). Therefore, the continuous body pieces 1b would come out from between, the cutting rollers 201, 202 with, of the two protruding portion bases 21b, 31b positioned at both end portions, the protruding portion bases 21b, 31b positioned on the downstream side along the transport direction in a temporarily joined state and the protruding portion bases 21b, 31b positioned on the upstream side along the transport direction not in a temporarily joined state, as shown in 14. FIG. 14 is a planar diagram showing the continuous body piece 1b.

<<Transportation Process (S003)>>

This process is carried out by the transportation device 300 shown in FIG. 10. The transportation device 300 receives whenever necessary the continuous body piece 1b from the cutting device 200 and transports this continuous body piece 1b in the transport direction toward a predetermined destination. Further, the transportation device 300 has the same configuration as that explained in the section on twisting of the band base material pieces 20b, 30b and includes a pair of belt conveyors 301, 302 positioned one over the other that sandwiches the entire continuous body piece 1b while transporting this continuous body piece 1b. When the continuous body piece 1b comes out from between the cutting rollers 201, 202 and advances between the belt conveyors 301, 302, moves in the transport direction between the belt conveyors 301, 302 and in the end, comes out from between the belt conveyors 301, 302.

Note that, when the continuous body pieces 1b move in the transport direction between the belt conveyors 301, 302, the band base material pieces 20b, 30b at the protruding portion bases 21b, 31b are in a temporarily joined state. In other words, the transportation process (S008) is a process that transports in the transport direction, the base materials (back-side band base material piece 20b, abdominal-side band base material piece 30b, main absorbent body base material 10a and the like) of the continuous body piece 1b in a state where the back-side band base material piece 20b and the abdominal-side band base material piece 30b are temporarily joined at the protruding portion bases 21b, 31b.

Further, in the present embodiment, of the two protruding portion bases 21b, 31b provided to the continuous body piece 1b, the base materials in the continuous body piece 1b are transported with tire protruding portion bases 21b, 31b positioned on the downstream side of the transport direction in a temporarily joined state. That is, of the two protruding portion bases 21b, 31b, the protruding portion base 21b, 31b that advances between the belt conveyors 301, 302 first and comes out from between the belt conveyors 301, 302 first as well is in a temporarily joined state.

Thereafter, diaper 1 as a product is completed from the continuous body piece 1b and this diaper 1 is inspected and packed to be shipped thereafter. Note that, in the present embodiment, the back-side band 20 and the abdominal-side band 30 are in a temporarily joined state at the protruding portions 21, 31. Therefore, when wearing the diaper 1, the wearer releases the temporarily joined state between the back-side band 20 and the abdominal-side band 30 to unfold (in a state shown in FIG. 1A) diaper 1 first and wears the diaper 1.

==Effectiveness of the Manufacturing Method of Diaper 1 According to the Present Embodiment==

According to the manufacturing method of diaper 1 described above, twisting of the back-side band base material piece 20b and the abdominal-side band base material piece 30b is prevented and allows stable manufacturing of diaper 1 provided with a desired quality. To be specific, as explained in the section on twisting of the band base material pieces 20b, 30b, the protruding portion bases 21b, 31b (corresponding to the portion where protruding portions 21, 31 are formed) at the location of the two ends of the band base material pieces 20b, 30b, is low in rigidity compared to the part that is overlapped with the main absorbent body base material 10a of the band base material pieces 20b, 30b thus is likely to be twisted. Therefore, when the continuous body piece 1b is transported in a state where the band base material pieces 20b, 30b are merely overlapped without joining, the previously discussed mouth opening phenomenon would occur (refer to FIG. 7).

Particularly, in the case the entire continuous body piece 1b is sandwiched between the pair of belt conveyors 301, 302 for this continuous body piece 1b to be transported as described above, if the end portion (particularly the end portion at the downstream side in the transport direction) of the band base material pieces 20b, 30b are twisted, it will be difficult for the continuous body piece 1b to enter between the above described belt conveyors 301, 302 (refer to FIG. 8). Further, at the time the continuous body piece 1b comes out from between the above-described belt conveyors 301, 302, if the end portions of the band base material pieces 20b, 30b are dragged by the belt conveyors 301, 302 and these end portions are twisted, it will be difficult for an appropriate process to be carried out in the following processes (for example, process for aligning diapers 1, process for inspecting the quality of the products).

With regard to this, in the present embodiment, the band base materials 20a, 30a are cut after temporarily joining the band base materials 20a, 30a together sit the protruding portion bases 21a, 31a. Thereafter, while the band base material pieces 20b, 30b are in a state temporarily joined at the protruding portion bases 21b, 31b, the continuous body piece 1b including the band base material pieces 20b, 30b and the main absorbent body base material 10a is transported. In this way, while the continuous body piece 1b is transported, an occurrence of the above described twisting is restrained allowing the continuous body piece 1b to be transported in a normal state. As a result of the above, the aforementioned problem will be solved.

Further in the present embodiment, in the process (S006) of temporarily joining the overlapped band base materials 20a, 30a, the back-side band base material 20a and the abdominal-side band base material 30a are temporarily joined at at least one of the two protruding portion bases 21a, 31a. And in the process (S008) of transporting the continuous body piece 1b in a state where the band base material pieces 20b, 30b are temporarily joined at the protruding portion bases 21b, 31b, the continuous body piece 1b is transported in a state where, of the two protruding portion bases 21b, 31b, the protruding portion bases 21b, 31b positioned at the downstream side in the transport direction is temporarily joined. When transporting the continuous body piece 1b, twisting is likely to occur at the protruding portion bases 21b, 31b at the downstream side in the transport direction. Therefore, at least the protruding portion bases 21b, 31b where twisting is likely to occur can be temporarily joined. Note that, taking into consideration the convenience at the time of wearing draper 1, it is desirable that the number of temporary joined, parts is kept to a minimum.

The method of manufacturing diaper 1 according to the present embodiment is a method of manufacturing diaper 1 including an elastic portion 18 that is provided to span from one end portion to the other end portion in the width direction of at least one of the back-side band 20 and the abdominal-side band 30, and that imparts elasticity to at least one of the aforementioned bands, and includes a process (S002) of joining the elastic portion base material 18a to at least one band base material of the back-side band base material 20a and the abdominal-side band base material 30a in the transport direction. Additionally, in the process (S005) of overlapping the band base materials 20a, 30a together, the back-side band base material 20a and the abdominal-side band base material 30a are overlapped with the elastic portion base material 13a joined to at least one of the band base materials 20a, 30a. Further, in the process (S006) of temporarily joining the overlapped band base materials 20a, 30a, the back-side band base material 20a and the abdominal-side band base material 30a are temporarily joined such that the temporary joining point at the protruding portion bases 21a, 31a avoids the joining point of the elastic portion base material 18a. In this way, the band base materials 20a, 30a can be temporarily joined together in a further appropriate manner. However, the temporary joining point can come to the joining point of the elastic portion base material 18a as long as appropriate temporary joining is realized.

In the process (3006) of temporarily joining the overlapped band base materials 20a, 30a together with the elastic portion 18 and the elastic portion base material 18a composed of an elastic string, the back-side band base material 20a and the abdominal-side band base material 30a are temporarily joined in an intermittent manner such that the temporary joining point in the protruding portion, bases 21a, 31a avoids the joining point of the elastic string. In this way, the temporary joining point can easily avoid the joining point of the elastic string and as a result allows the band base materials 20a, 30a to be temporary joined more appropriately. However, temporary joining in an intermittent manner can be performed when joining the band base materials 20a, 30a together in the direction intersecting the transformation direction. Additionally, the elastic portion 18 and the elastic portion base material 18a can be formed with material (for example, band-shaped elastic) besides elastic strings.

Further the method of producing diaper 1 according to the present embodiment is a method of producing diaper 1 including connection piece 40 that is attached to the protruding portion 21 of the back-side band 20 and connects the back-side band 20 with the abdominal-side band 30 when worn, and includes a process (S003) of joining the connection piece base material 40a to the protruding portion base 21a of the back-side band base material 20a. In the process (S005) of overlapping the band base materials 20a, 30a together, the back-side band base material 20a and the abdominal-side band base material 30a are overlapped such that the connection piece base material 40a is sandwiched between the protruding portion base 21a of the back-side band base material 20a and the protruding portion base 31a of the abdominal-side band base material 30a. And in the process (S006) of temporarily joining the overlapped band base materials 20a, 30a together, the back-side band base material 20a and the abdominal-side band base material 30a are temporarily joined such that the temporary joining point in the protruding portion bases 21a, 31a avoids the part where the connection piece base material 40a is sandwiched. In this way, the band base materials 20a, 30a can be temporarily joined together in a more appropriate manner.

Regarding the part where the connection piece base material 40a is sandwiched, if temporary joining is performed to the part where the fold back portion 43a (refer to FIG. 6D) of the connection piece base material 40a is attached to the protruding portion base 21a of the back-side band base material 20a, this part would become rigid and would give the skin of the wearer a stiff sense when wearing diaper 1. Whereas if temporary joining is provided to the part away form the part where the connection piece base material 40a is sandwiched, the above-described situation can be avoided.

Specifically, at the time diaper 1 is completed, the portion corresponding to the temporary joining point comes to a position outside the connection piece 40 in the width direction. And when diaper 1 is in a worn state (that is when in the state shown in FIGS. 2A and 2B), the end portion on the outside in the width direction of the connection piece 40 intervenes between the portion corresponding to the above-described temporary joining point and the wearer's skin. In other words, the portion corresponding to the above-described temporary joining point does not touch the wearer's skin when diaper 1 is worn so that a stiff sense would not be given to the wearer. In this way, when the temporary joining point is at a point away from the point sandwiched between the connection piece base material 40a and the band base materials 20a, 30a are temporarily joined together so that the part corresponding to the temporary joining point does not touch the wearer's skin when wearing diaper 1 as well, the quality of diaper 1 can be improved.

Other Embodiments

In the above-described embodiment (hereafter present example), the device for temporary joining 100 and the cutting device 200 are positioned at locations different from each other in the transport direction, and description was given on forms of implementing, at locations different from each other in the transport direction, the process of temporary joining the band base materials 20a, 30a together and the process of cutting the temporarily joined band base materials 20a, 30a. However, different from the present example, a form of implementing the above-described two processes (hereafter modified example), for example, on the same member is possible. In the following, description on the modified example will be given. Note that, explanation on parts that are the same as the present example will be omitted.

Figure 15:
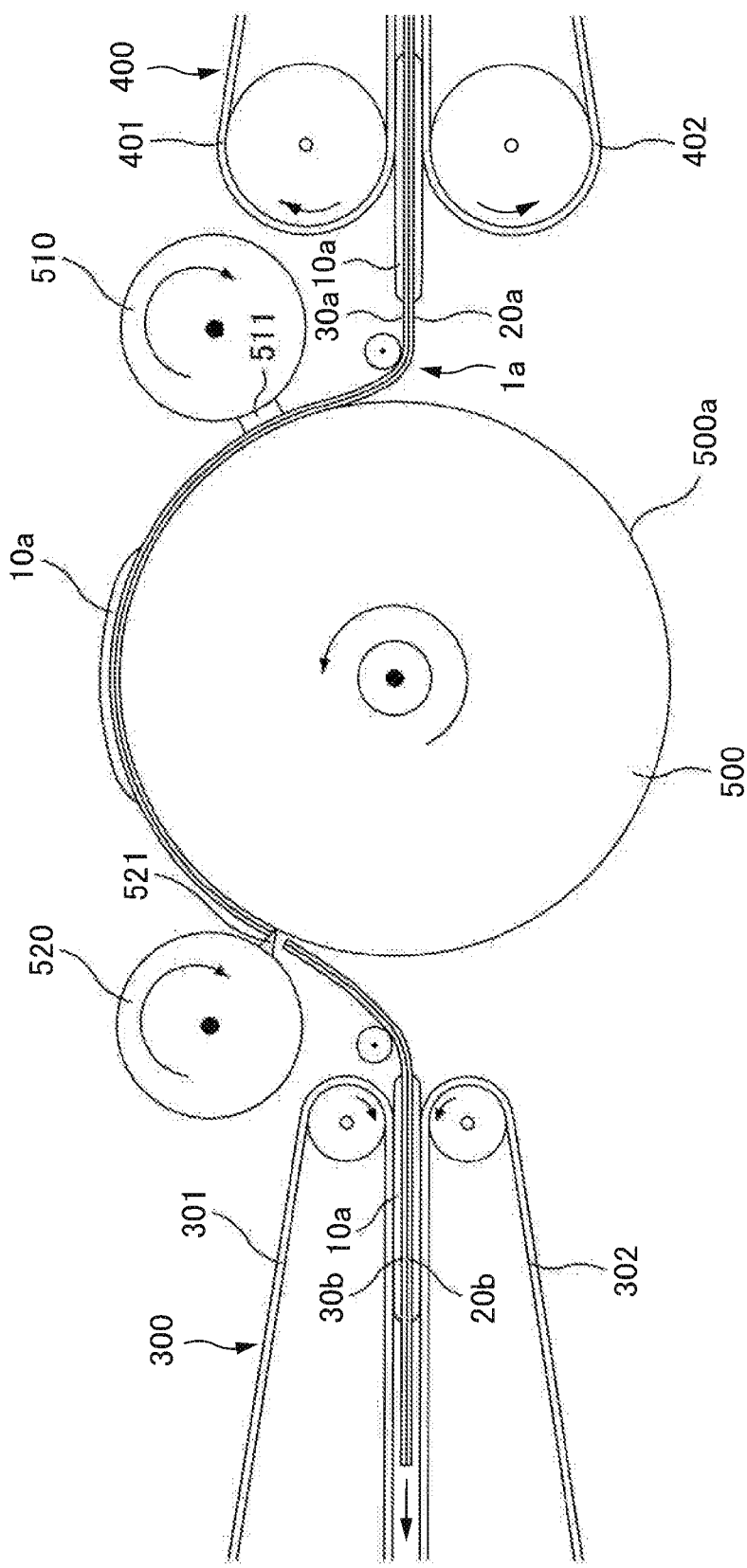
FIG. 15 is a schematic diagram of the manufacturing line of diaper 1 according to a modified example.

In the present modified example, as shown in FIG. 15, a rotatable roller 500 rotatably supported about an axis perpendicular to the transport direction of the continuous body 1a is disposed between the transportation device 400 on the upstream side in the transport direction and the transportation device 300. FIG. 15 is a schematic diagram of the manufacturing line of diaper 1 according to the modified example. The rotatable roller 500 receives the continuous body 1a from the upstream side transportation device 400 on the outer circumferential surface 500a, and the rotatable roller 500 rotates while the overlapped back-side band base material 20a and the abdominal-side band base material 30a are in a state laid on the outer circumferential surface 500a. In this way, the continuous body 1a including the band members 20a, 30a would move along in the rotation direction of the rotatable roller 500. Further, the rotatable roller 500 delivers the continuous body piece 1b formed from the continuous body 1a to the transportation device 300.

Then in the modified example, while the continuous body 1a is laid on the outer circumferential surface 500a of the rotatable roller 500, a process of temporarily joining the band base materials 20a, 30a together, and a process of cutting the temporarily joined band base materials 20a, 30a are both carried out. In other words, the temporary joining location where the band base materials 20a, 30a are temporarily joined together and the cutting location at which the temporarily joined band base materials 20a, 30a are cut, are located on the above-described outer circumferential surface 500a.

To be specific, as shown in FIG. 15, the roller for temporary joining 510 and the cutter roller 520 are positioned along the rotation direction of the rotatable roller 500. The roller for temporary joining 510 has a configuration approximately the same as the aforementioned roller for temporary joining 101 and includes a lump 511 on the outer circumferential surface thereof. And this lump 511 and the outer circumferential surface 500a of the rotatable roller 500 sandwiches therebetween the band base materials 20a, 30a to temporarily join the band base materials 20a, 30a together by embossing. The cutter roller 520 has a configuration approximately the same as the aforementioned cutting roller 201 and includes a blade 521 on its outer circumferential surface. This blade 521 and the outer circumferential surface 500a of the rotatable roller 500 sandwiches therebetween the temporarily joined band base materials 20a, 30a and cuts the band base materials 20a, 30a.

With the above configuration, while the rotatable roller 500 rotates and the continuous body 1a moves in the rotation direction, embossing is performed by the roller for temporary joining 510 to the two overlapped band base materials 20a, 30a in a state laid on the outer circumferential surface 500a of the rotatable roller 500. In this way, the band base materials 20a, 30a are temporarily joined together. Thereafter, when the continuous body 1a is moved in the rotation direction by a further rotation of the rotatable roller 500, the temporarily joined band base materials 20a, 30a are cut by the blade 521 of the cutter roller 520 at a predetermined point (point where the cutting line is positioned). In this way, band base material pieces 20b, 30b are formed from the band base materials 20a, 30a (in other words, continuous body piece 1b is formed from continuous body 1a).

The continuous body piece 1b is delivered to the transportation device 300 after moving in the rotation direction by a further rotation of the rotatable roller 500. Thereafter, the continuous body piece 1b continues to be transported in the downstream side in the transport direction with, of the two protruding portion bases 21b, 31b, the protruding portion base 21b, 31b positioned on the downstream side in the transport direction in a state temporarily joined.

In the above description on the modified example, when the overlapped band base materials 20a, 30a are joined together, the rotatable roller 500 rotated in a state with the back-side band base material 20a and the abdominal-side band base material 30a laid over the outer circumferential surface 500a of the rotatable roller 500, makes the protruding portion bases 21a, 31a move to the temporary joining position, in the rotation direction of the rotatable roller 500, and then the two band base materials 20a, 30a are temporarily joined at the protruding portion bases 21a, 31a. Further, when cutting the temporarily joined band base materials 20a, 30a, the rotatable roller 500 is further rotated with the back-side band base material 20a and the abdominal-side band base material 30a laid over the outer circumferential surface 500a to thereby move the protruding portion bases 21a, 31a from the temporary joining position to the cutting position in the rotation direction to cut the two band base materials 20a, 30a at the end (location of the cutting line) of the protruding portion bases 21a, 31a.

As described above, different from the present example, the modified example has the temporary joining position and the cutting position defined on a same member (specifically, on the outer circumferential surface 500a of the rotatable roller 500). Therefore, positional displacement of the temporary joining point and the cutting point on the continuous body 1a can be suppressed. The modified example is in a more preferred form in this regard. Meanwhile, when considering the ease of maintenance of the device, it is preferable that the device for temporary joining 100 and the cutting device 200 are separated so that the temporary joining position and the cutting position are placed apart, and to this point, the present example is in a more preferred form.

Note that, the modified example is the same as the present example besides the above-mentioned differences and offers the same operational advantages as the present example.

Other Embodiments

In the foregoing embodiments, the method for manufacturing diaper 1 (absorbent article) according to the present invention was mainly described however, the above-described embodiment is intended to facilitate the understanding of the present invention but not to limit the invention. It is needless to say that modifications and improvements of the present invention are possible without departing from the scope of the invention, and equivalents thereof are also encompassed by the invention. Further, the above-mentioned set values, dimensional values, shapes and the like are merely examples for exercising the effects of the present invention but not to limit the invention.

In the foregoing embodiment, at the time diaper 1 is shipped, the back-side band 20 and the abdominal-side band 30 are temporarily joined at the protruding portions 21, 31 and the temporarily joined state was released when wearing the diaper 1 however, for example, the temporarily joined state can be released after the continuous body piece 1b is transported by the transportation device 300 and immediately before the completion of diaper 1.

Additionally, in the foregoing embodiment, the band base materials 20a, 30a were temporarily joined by heat press embossing however, the present invention is not limited to such and other temporary joining methods such as adhesion methods using ultrasound waves, methods using hot-melt type adhesives, and the like can be used.

Further, in the foregoing embodiment, the band base materials 20a, 30a continuous in a web (strip) form were transported in a spaced apart and parallel aligned state however, the present invention is not limited to such. The band base materials 20a, 30a need not be in a band form as long as they are transported in a continuous state.

Furthermore, in the foregoing embodiment, the continuous body piece 1b was transported with this continuous body piece 1b sandwiched between a pair of belt conveyors 301, 302 however, the present invention is not limited to such and other transportation devices (for example, a belt conveyor that transports the continuous body piece 1b placed thereon, a transportation roller that rotates while retaining the continuous body piece 1b on its circumferential surface) can be used.

Even furthermore, in the foregoing embodiment an open-type diaper 1 was given as an example for explaining the manufacturing method thereof however, the present invention can be applied to the manufacturing method of wear-on type (so-called pants-type) diapers. Further, as long as it is an absorbent article including a main absorbent body 10, a back-side band 20 and a abdominal-side band 30 and two protruding portions 21, protruding from both ends of the main absorbent body 10 in the direction intersecting the longitudinal direction of the main absorbent body 10, are formed to the back-side band 20 and the abdominal-side band 30, respectively, the present invention can be applied to manufacturing methods of other absorbent articles.

REFERENCE SIGNS LIST 1 diaper, 1a continuous body, 1b continuous body piece, 2 body encircling opening, 3 leg encircling opening, 4 gather portion around the leg, 10 main absorbent body, 10a main absorbent body base material, 11 absorbent body, 12 top sheet member, 13 backsheet member, 14 leakproof sheet, 15 cover sheet, 16 liquid permeable sheet, 17 gather forming member, 18 elastic portion, 18a elastic portion base material, 18b elastic portion base material piece, 20 back-side band, 20a back-side band base material, 20b back-side band base material piece, 21 protruding portion, 21a, 21b protruding portion base (a part where a protruding portion is formed), 30 abdominal-side band, 30a abdominal-side band base material, 30b abdominal-side band base material piece, 31 protruding portion, 31a, 31b protruding portion base (a part where a protruding portion is formed), 40 connection piece, 40a connection piece base material, 41 fastening tape, 42 stiffening sheet, 43 end portion on the fixed end side, 43a fold back portion, 44 perforation, 50 target tape, 50a target tape base material, 50b target tape base material piece, 100 device for temporary joining, 101, 102 rollers for temporary joining, 103 lump, 200 cutting device, 201, 202 rollers for cutting, 203 blade, 300 transportation device, 301, 302 belt conveyor, 400 upstream side transportation device, 401, 402 belt conveyor, 500 rotatable roller, 500a outer circumferential surface, 510 roller for temporary joining, 511 lump, 520 cutter roller, 521 blade

The invention claimed is:

1. A method of manufacturing an absorbent article, the absorbent article including:

a main absorbent body having an absorbent body configured to absorb liquid and to be put against a crotch of a wearer when worn, a back-side band that intersects the main absorbent body at one longitudinal end portion of the main absorbent body, and that is configured to be positioned on a back side of the wearer when worn, and an abdominal-side band that intersects the main absorbent body at another longitudinal end portion of the main absorbent body, and that is configured to be positioned on an abdominal side of the wearer when worn, wherein each of the back-side band and the abdominal-side band includes two protruding portions that protrude from both ends of the main absorbent body in a transverse direction intersecting the longitudinal direction of the main absorbent body, the method comprising:

joining, during transportation of a continuous back-side band base material and a continuous abdominal-side band base material in a transport direction, one longitudinal end portion of a main absorbent body base material to the back-side band base material and another longitudinal end portion of the absorbent body base material to the abdominal-side band base material, so that the longitudinal direction of the main absorbent body base material intersects the transport direction;

folding the main absorbent body base material and overlapping the back-side band base material with the abdominal-side band base material;

temporarily joining the overlapped back-side band base material and abdominal-side band base material only at, of first and second portions where the two protruding portions are to be formed, the first portion positioned downstream of the second portion in the transport direction;

cutting the temporarily joined back-side band base material and abdominal-side band base material and forming a back-side band base material piece and an abdominal-side band base material piece; and transporting the back-side band base material piece, the abdominal-side band base material piece and the main absorbent body base material in the transport direction while the back-side band base material piece and the abdominal-side band base material piece are in a temporarily joined state only at the first portion.

2. The method according to claim 1, wherein
the absorbent article further includes an elastic portion that is spanned from one end portion to another end portion in the transverse direction of at least one band of the back-side band and the abdominal-side band, and that is configured to impart elasticity to the at least one band, the method further includes:
   joining, along the transport direction, an elastic portion base material, to at least one base band material of the back-side band base material and the abdominal-side band base material at a joining point,
in said overlapping, the back-side band base material is overlapped with the abdominal-side band base material in a state where the at least one band material is joined to the elastic portion base material, and
in said temporarily joining, the back-side band base material and the abdominal-side band base material are temporarily joined at a temporary joining point of the first portion so that the temporary joining point avoids the joining point of the elastic portion base material.

3. The method according to claim 2, wherein
the elastic portion base material includes an elastic string, and
said temporary joining of the back-side band base material and the abdominal-side band base material is performed intermittently in a cross direction intersecting the transport direction so that the temporary joining point of the first portion avoids the joining point of the elastic string.

4. The method according to claim 1, wherein
the absorbent article includes a connection piece that is attached to the protruding portions of the back-side band and configured to connect the back-side band and the abdominal-side band when worn,
the method further includes:
   joining a connection piece base material to a portion of the back-side band base material where the protruding portions of the back-side band is are to be formed,
in said overlapping, the back-side band base material is overlapped with the abdominal-side band base material so that the connection piece base material is sandwiched between the back-side band base material and the abdominal-side band base material at the first and second portions where the protruding portions of the back-side band are to be formed, and
in said temporarily joining, the back-side band base material and the abdominal-side band base material are temporarily joined at a temporary joining point of the first portion so that the temporary joining point avoids a point where the connection piece base material is sandwiched between the back-side band base material and the abdominal-side band base material.

5. The method according to claim 1, further comprising:
moving the first portion in a rotation direction of a rotatable roller to a temporary joining position where the back-side band base material and the abdominal-side band base material are temporarily joined, by rotating the rotatable roller while the back-side band base material and the abdominal-side band base material are on an outer circumferential surface of the rotatable roller, and
moving the first portion in the rotation direction from the temporary joining position to a cutting position where the back-side band base material and the abdominal-side band base material are cut in said cutting, by rotating the rotatable roller,
wherein the back-side band base material and the abdominal-side band base material are cut in said cutting at ends of the first and second portions to obtain the protruding portions.

6. A method of manufacturing an absorbent article, the absorbent article including: a main absorbent body having an absorbent body configured to absorb liquid, a back-side band and an abdominal side band attached to the main absorbent body at two longitudinal end portions of the main absorbent body, respectively, wherein each of the back-side band and the abdominal-side band includes two protruding portions that protrude from both ends of the main absorbent body in a transverse direction intersecting the longitudinal direction of the main absorbent body, said method comprising:
   transporting a continuous back-side band base material and a continuous abdominal side base material in a transport direction;
   joining, during said transporting, one longitudinal end portion of a main absorbent body base material to the back-side band base material and another longitudinal end portion of the absorbent body base material to the abdominal-side band base material, so that the longitudinal direction of the main absorbent body base material intersects the transport direction;
   folding the main absorbent body base material to overlap the back-side band base material with the abdominal-side band base material in the longitudinal direction, wherein the overlapped back-side band base material and abdominal-side band base material have first and second portions where the two protruding portions are to be formed, and the first portion is positioned downstream of the second portion in the transport direction;

temporarily joining the overlapped back-side band base material and abdominal-side band base material at the first portion, but not at the second portion; and cutting the temporarily joined back-side band base material and abdominal-side band base material to obtain a back-side band base material piece and an abdominal-side band base material piece.

7. The method according to claim 6, wherein said temporarily joining the overlapped back-side band base material and abdominal-side band base material comprises embossing the overlapped back-side band base material and abdominal-side band base material at the first portion.

8. The method according to claim 6, wherein the overlapped back-side band base material and abdominal-side band base material are temporarily joined at a temporary joining point of the first portion.

9. The method according to claim 8, further comprising:
joining, before said folding, an elastic portion base material to at least one base band material of the back-side band base material and the abdominal-side band base material along the transport direction at a joining point, wherein said joining point does not overlap with the temporary joining point of the first portion.

10. The method according to claim 8, wherein, in said temporarily joining, the overlapped back-side band base material and abdominal-side band base material are temporarily joined together at a plurality of temporary joining points, and the plurality of temporary joining points are intermittently arranged in a cross direction intersecting the transport direction.

11. The method according to claim 8, further comprising:
joining, before said folding, a connection piece base material to a point of one of the first and second portions of the back-side band base material, wherein said point does not overlap the temporary joining point.

12. The method according to claim 6, wherein said temporarily joining is performed after said folding the main absorbent body base material.

13. The method according to claim 6, wherein said temporarily joining and said cutting are performed while the overlapped back-side band base material and abdominal-side band base material are rotated by a rotatable roller in a rotation direction thereof.

14. The method according to claim 6, further comprising:
transporting the overlapped back-side band base material piece and abdominal-side band base material piece with the folded main absorbent body base material in the transport direction while the back-side band base material piece and the abdominal-side band base material piece are temporarily joined at the first portion but not at the second portion.

* * * * *